(12) United States Patent  (10) Patent No.: US 8,465,330 B2
Miyagi et al.  (45) Date of Patent: Jun. 18, 2013

(54) CONNECTOR FOR MEDICAL INSTRUMENT

(75) Inventors: Masaaki Miyagi, Hino (JP); Kazuhiko Hino, Hachioji (JP); Takeshi Ogura, Hamburg (DE); Hidenobu Kimura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/446,112

(22) Filed: Apr. 13, 2012

(65) Prior Publication Data

US 2012/0202385 A1  Aug. 9, 2012

Related U.S. Application Data

(63) Continuation of application No. PCT/JP2010/068196, filed on Oct. 15, 2010.

(30) Foreign Application Priority Data

Oct. 28, 2009  (JP) .................................. 2009-248263

(51) Int. Cl.
  *H01R 13/502* (2006.01)
  *H01R 13/514* (2006.01)
(52) U.S. Cl.
  USPC ............................ 439/701; 439/460; 439/248
(58) Field of Classification Search
  USPC .................. 439/701, 246–248, 470, 460–462
  See application file for complete search history.

(56) References Cited

U.S. PATENT DOCUMENTS

| 6,582,248 B2* | 6/2003 | Bachman ...................... 439/462 |
| 6,755,691 B2* | 6/2004 | Sasame et al. ................ 439/247 |
| 2008/0039689 A1 | 2/2008 | Yoshimitsu et al. |
| 2008/0281157 A1 | 11/2008 | Miyagi et al. |
| 2008/0281158 A1 | 11/2008 | Miyagi et al. |

FOREIGN PATENT DOCUMENTS

| EP | 1 990 871 A2 | 11/2008 |
| JP | 08-211307 | 8/1996 |
| JP | 2004-275495 | 10/2004 |
| JP | 2006-095260 | 4/2006 |
| JP | 2008-278971 | 11/2008 |

OTHER PUBLICATIONS

European Search Report dated Jul. 6, 2012 from corresponding European Patent Application No. EP 10 82 6542.2.
International Search Report dated Nov. 9, 2010 issued in PCT/JP2010/068196.

* cited by examiner

*Primary Examiner* — Felix O Figueroa
(74) *Attorney, Agent, or Firm* — Scully, Scott, Murphy & Presser, P.C.

(57) ABSTRACT

A connector for a medical instrument connected to an external device for medical use is provided, and the connector for a medical instrument includes a plug portion in which electric contact point portions are placed, outer sheath cases connectively provided at the plug portion, a sub frame member interposed between the plug portion and the outer sheath cases, and having a flange portion, and a main frame member housed in the outer sheath cases and fixed to the sub frame member, wherein the plug portion and the outer sheath cases are butted against the flange portion by different fixing members respectively, and are compressed and fixed to the sub frame member.

10 Claims, 27 Drawing Sheets

CONNECTOR FOR MEDICAL INSTRUMENT

CROSS REFERENCE TO RELATED APPLICATION

This application is a continuation application of PCT/JP2010/068196 filed on Oct. 15, 2010 and claims benefit of Japanese Application No. 2009-248263 filed in Japan on Oct. 28, 2009, the entire contents of which are incorporated herein by this reference.

BACKGROUND OF THE INVENTION

1. Field of the Invention

The present invention relates to a connector for a medical instrument provided in a medical instrument to be connected to a peripheral apparatus.

2. Description of the Related Art

An endoscope apparatus, which is a medical instrument, is connected to a video processor, a light source apparatus and the like, which are peripheral apparatuses. Therefore, in an endoscope apparatus, an endoscope connector which can be detachably connected to a video processor, a light source apparatus and the like is placed at an extension end of a signal cable. The endoscope connector is connected to the video processor, the light source apparatus and the like, which are external devices, any number of times.

The endoscope connector as above is disclosed in an electronic endoscope described in, for example, Japanese Patent Application Laid-Open Publication No. 8-211307. The electronic endoscope reduces noise emission by being provided with a cylindrical ferrite core at a connection portion in a bend preventer which is placed in the vicinity of a terminal end of a connection cord to which the endoscope connector is connected, in order to reduce noise emission and the like from the signal cable and to prevent peripheral apparatuses and the like from being misoperated.

SUMMARY OF THE INVENTION

A connector for a medical instrument according to an aspect of the present invention is a connector for a medical instrument connected to an external device for medical use, and includes a plug portion in which a plurality of electric contact point portions to the external device are placed, an outer sheath case having a substantially cylindrical shape and connectively provided at the plug portion, a disk-shaped frame member interposed between the plug portion and the outer sheath case, and having a flange portion which abuts on respective circumferential end portions of the plug portion and the outer sheath case, and a main frame member housed in the outer sheath case and fixed to the disk-shaped frame member, wherein the plug portion and the outer sheath case receive pressure generated by being butted against the flange portion by fastening of different fixing members respectively, and are fixed to the disk-shaped frame member in a state in which the plug portion and the outer sheath case are compressed in same longitudinal axis directions.

DETAILED DESCRIPTION OF THE PREFERRED EMBODIMENTS

Hereinafter, an endoscope apparatus which is the present invention will be described. It should be noted that in the following description, the drawings based on each embodiment are schematic, and the relation of the thickness and the width of each portion, the ratio of the thicknesses of the respective portions and the like differ from the actual relation, the ratio and the like. The portions where the relations and the ratios of the mutual sizes differ from one another may be included among the drawings.

First, one embodiment of the present invention will be described based on the drawings.

Figure 1:
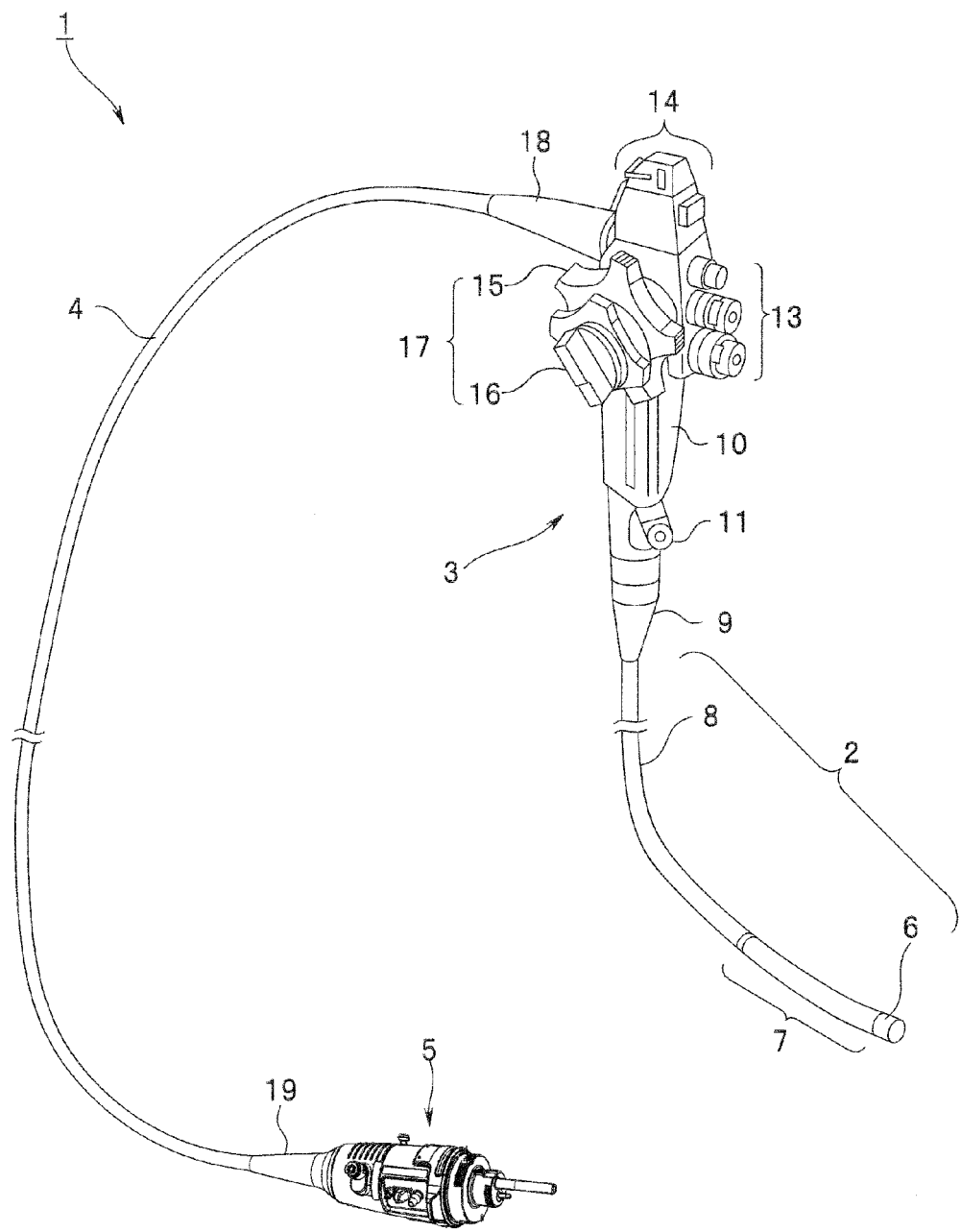
FIG. 1 relates to a first embodiment of the present invention, and is a perspective view showing an entire configuration of an endoscope apparatus.
Figure 2:
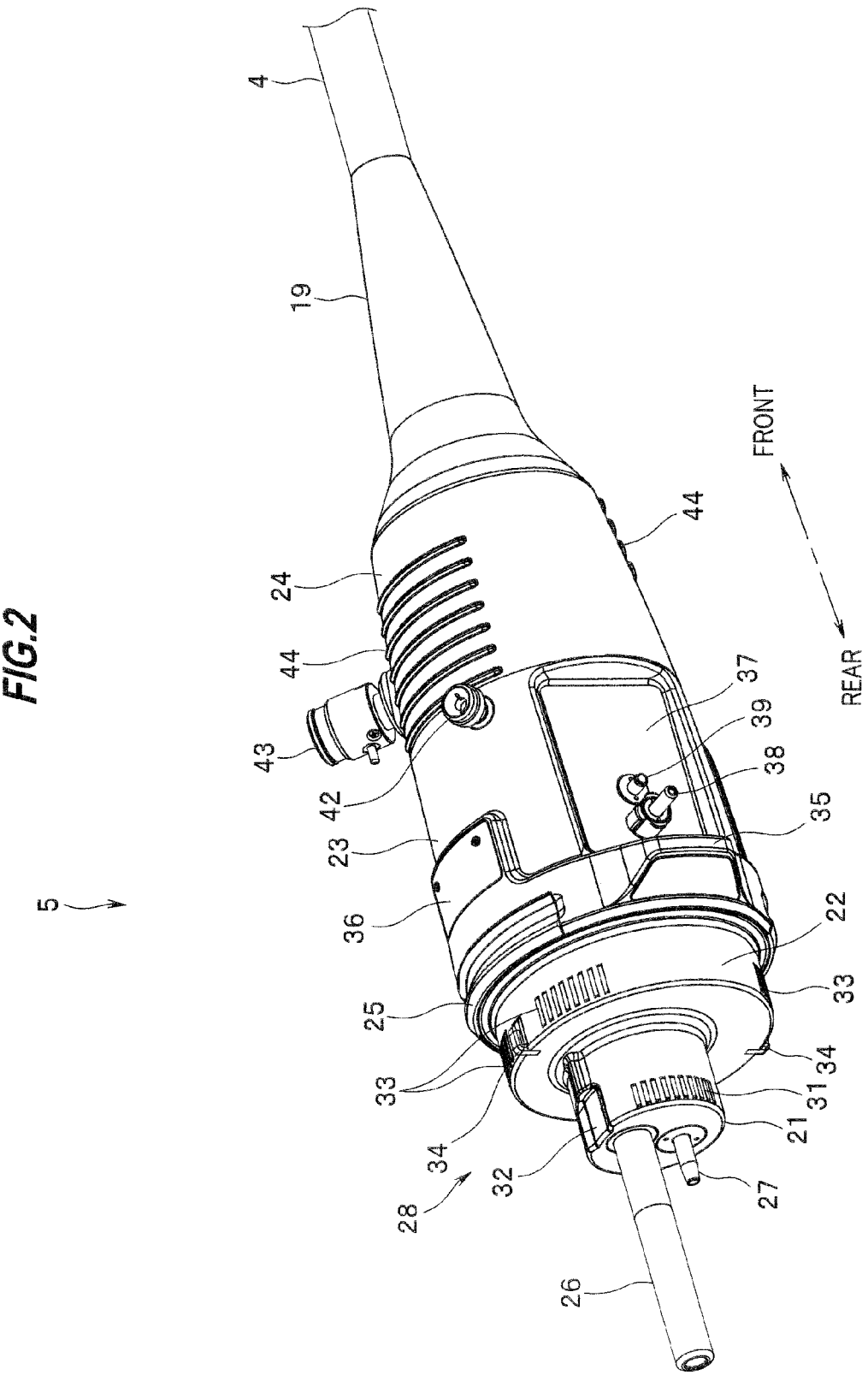
FIG. 2 relates to the first embodiment of the present invention, and is a perspective view showing a configuration of an endoscope connector.
Figure 3:
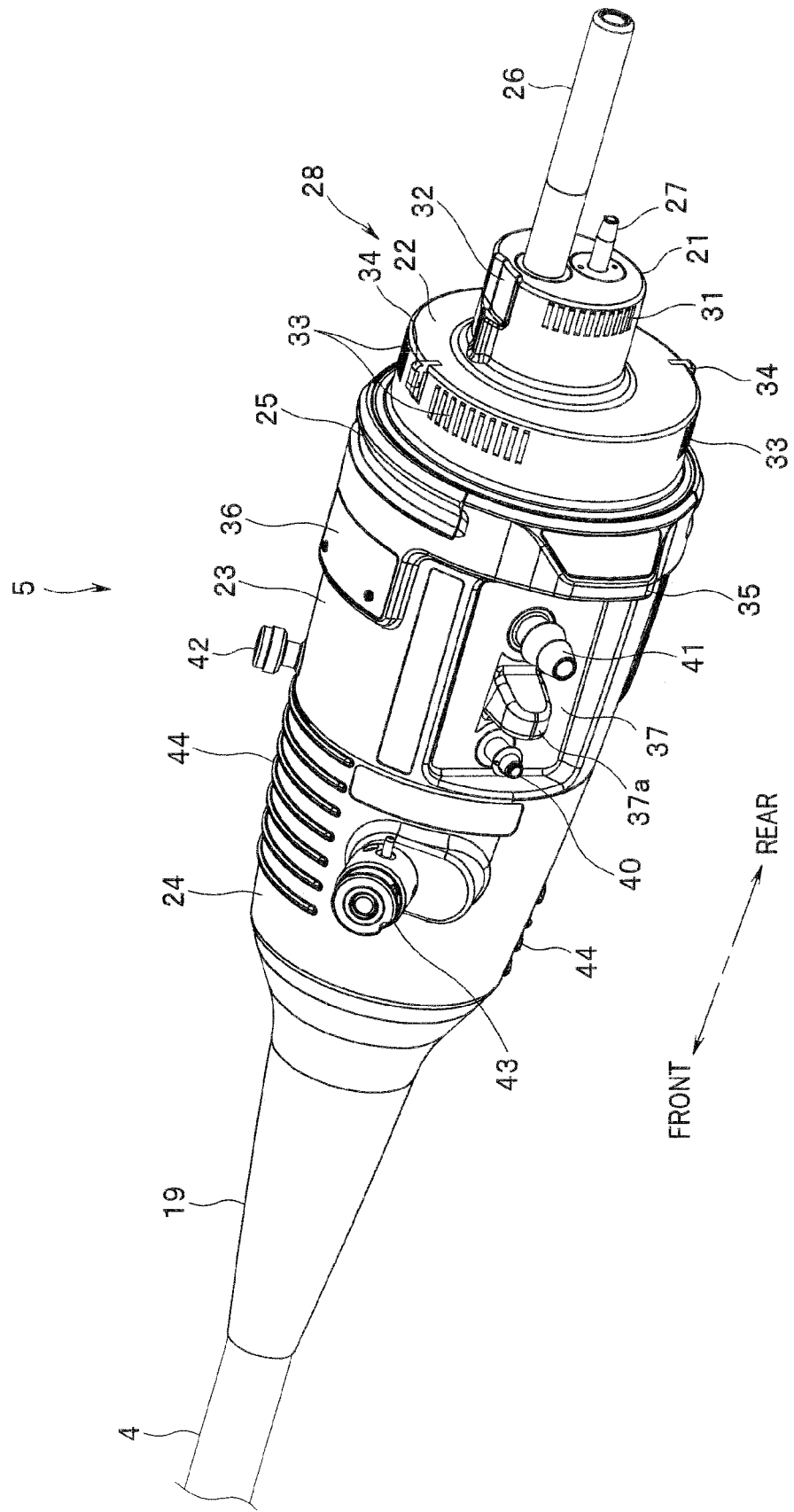
FIG. 3 relates to the first embodiment of the present invention, and is a perspective view of the configuration of the endoscope connecter at an angle different from FIG. 2.
Figure 4:
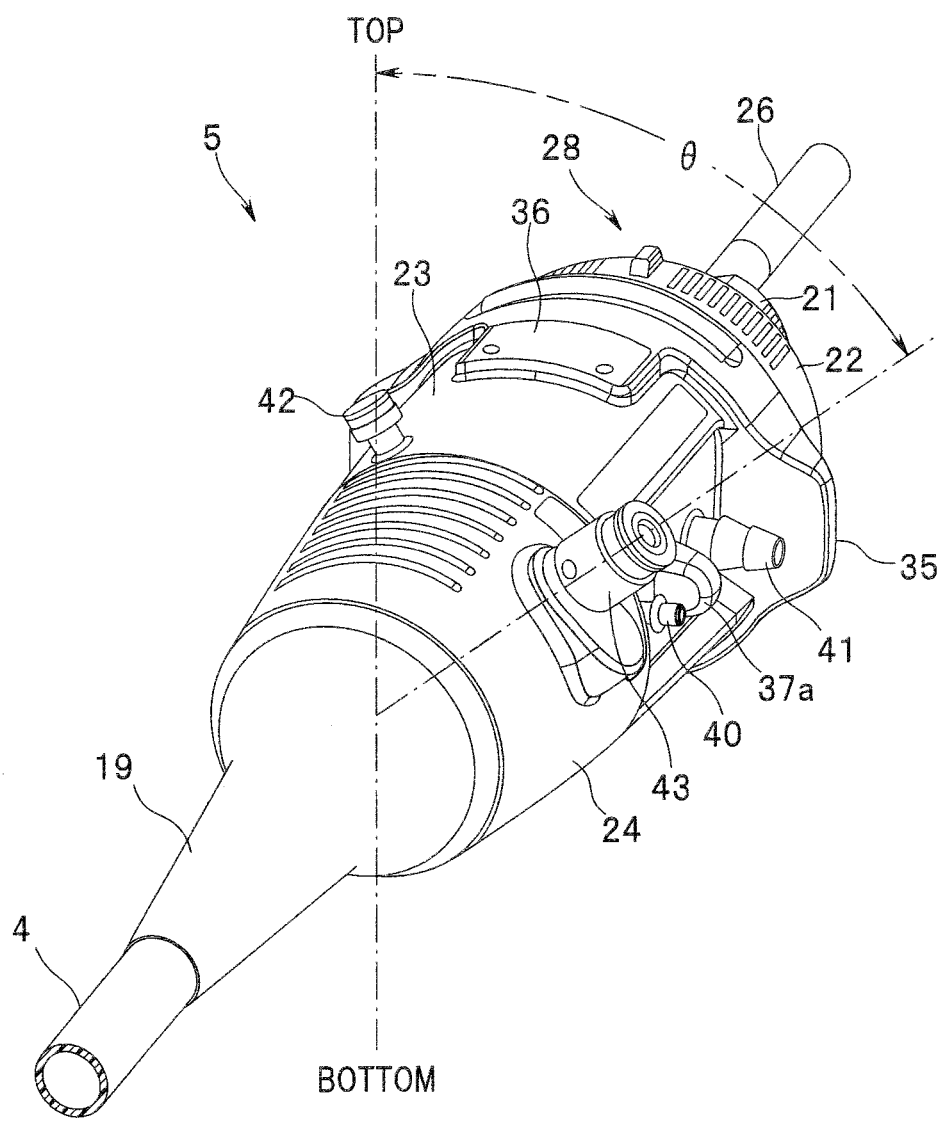
FIG. 4 relates to the first embodiment of the present invention, and is a perspective view showing the configuration of the endoscope connecter seen from a front side.
Figure 5:
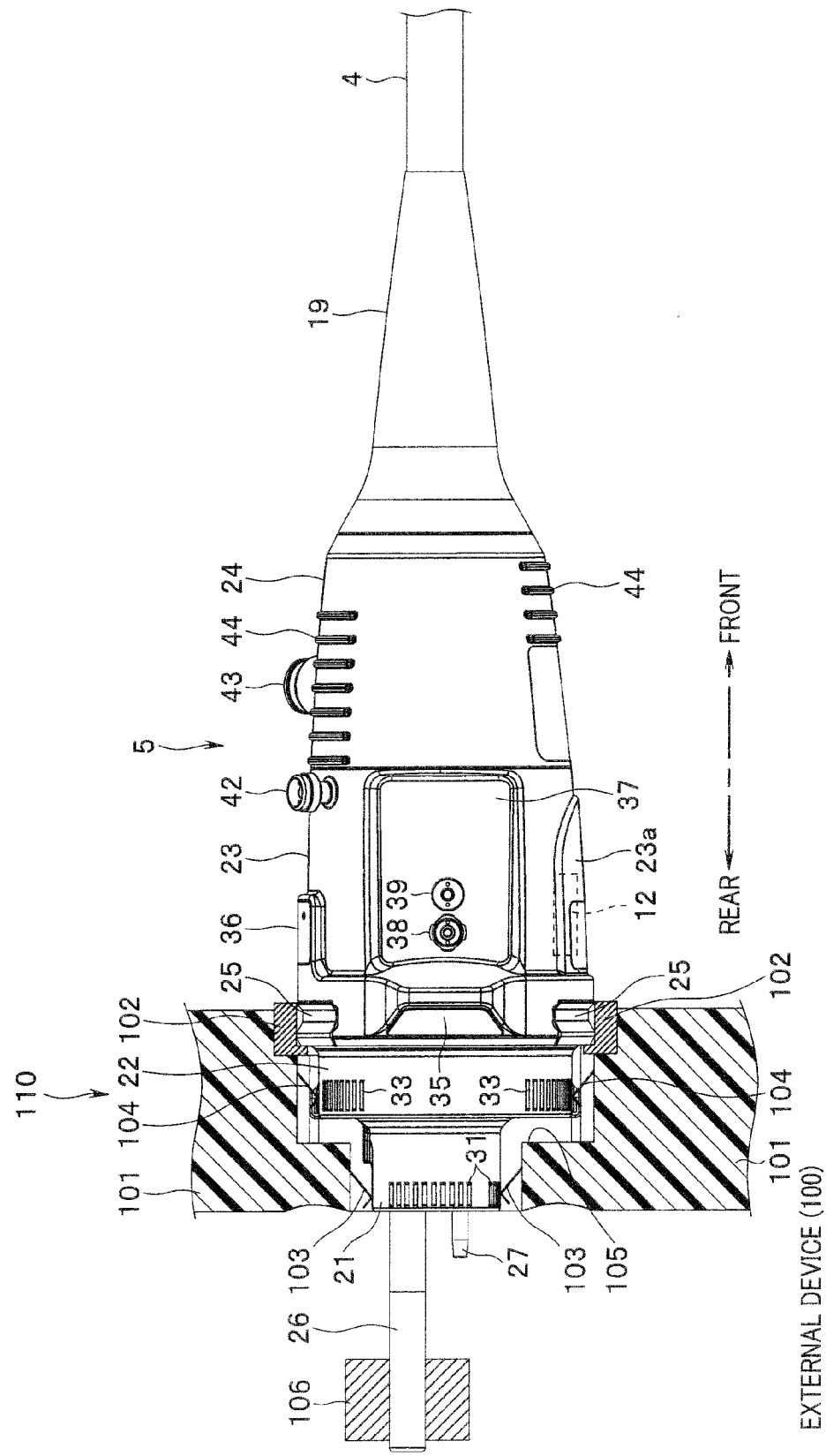
FIG. 5 relates to the first embodiment of the present invention, and is a partial cross-sectional view showing the configuration of the endoscope connector connected to an external device.
Figure 6:
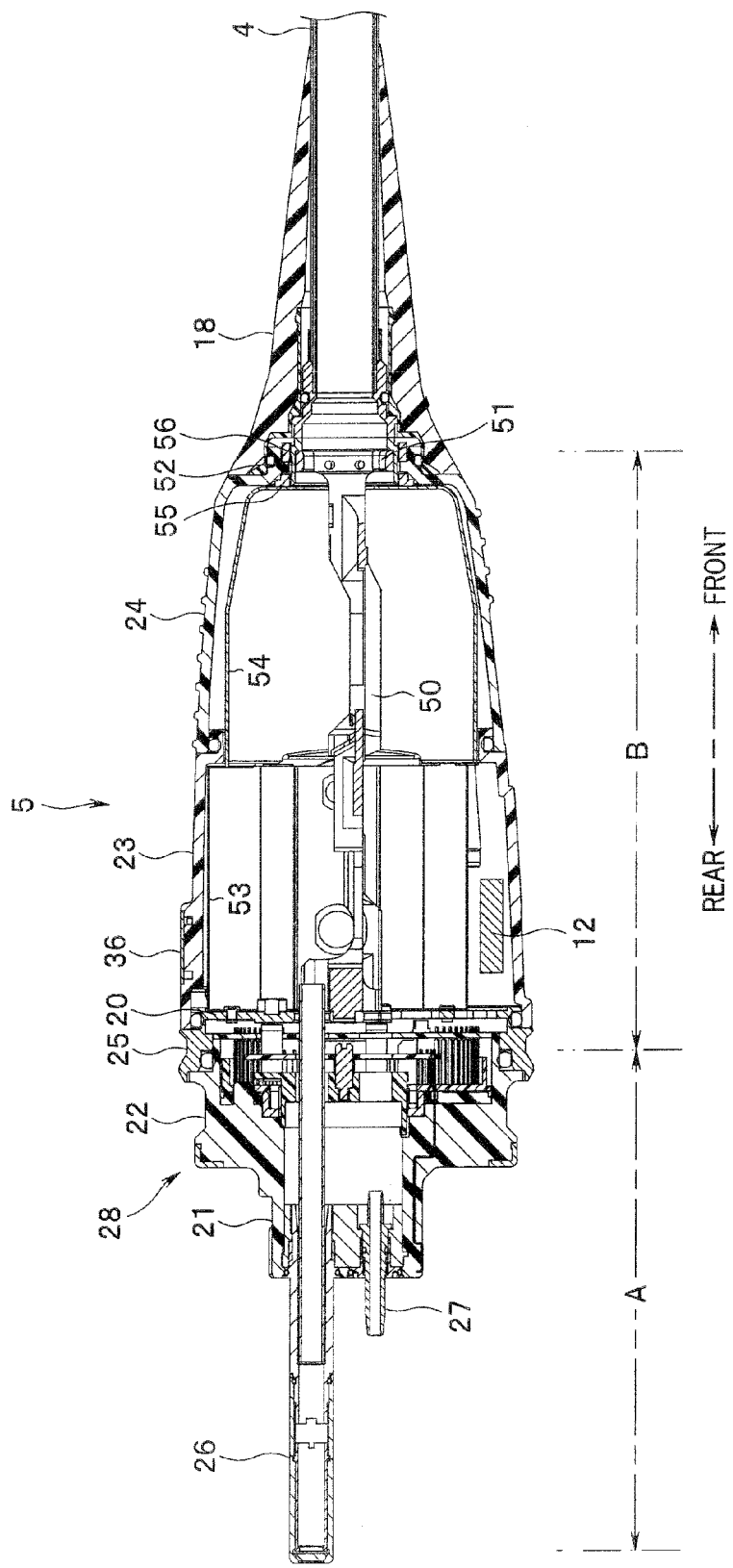
FIG. 6 relates to the first embodiment of the present invention, and is a sectional view showing the configuration of the endoscope connector.
Figure 7:
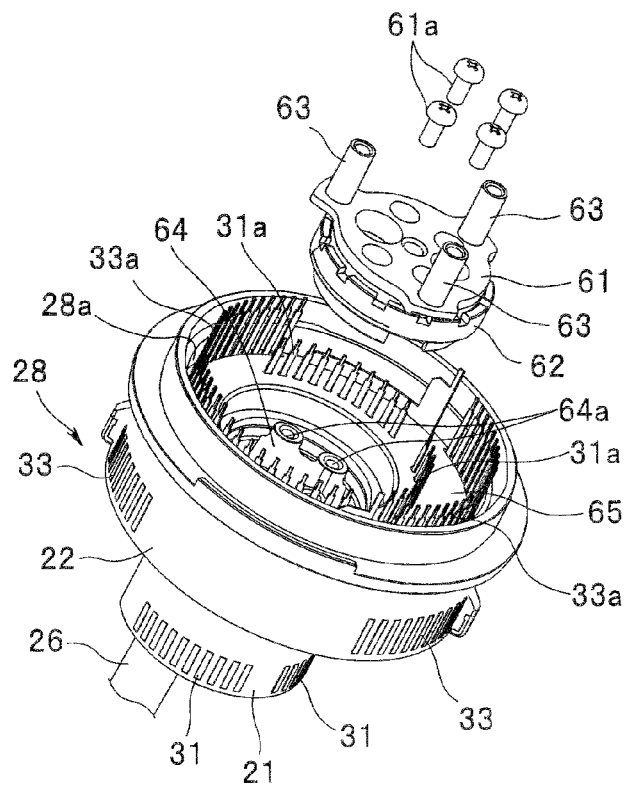
FIG. 7 relates to the first embodiment of the present invention, and is an exploded perspective view showing a configuration in which a support plate is fixed to an electric plug portion.
Figure 8:
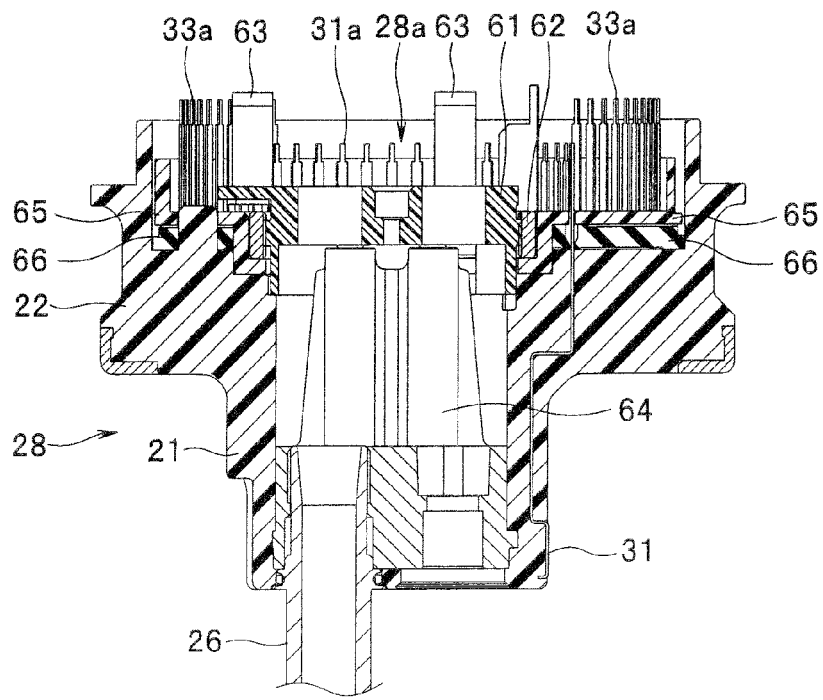
FIG. 8 relates to the first embodiment of the present invention, and is a sectional view showing a configuration of the electric plug portion to which the support plate is fixed.
Figure 9:
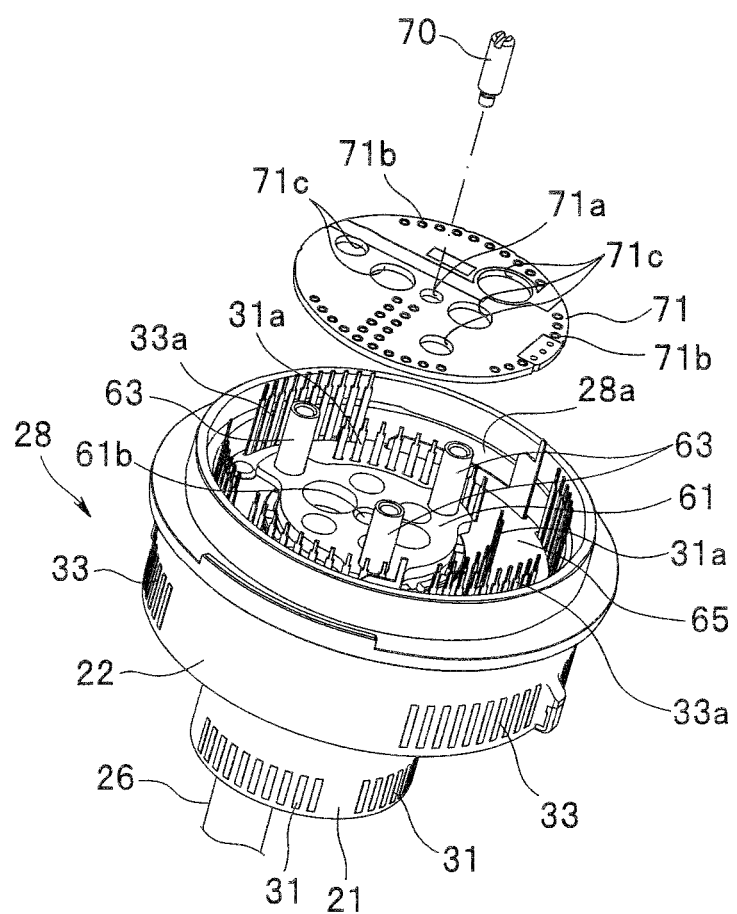
FIG. 9 relates to the first embodiment of the present invention, and is an exploded perspective view showing a configuration in which a first board is connected to the electric plug portion.
Figure 10:
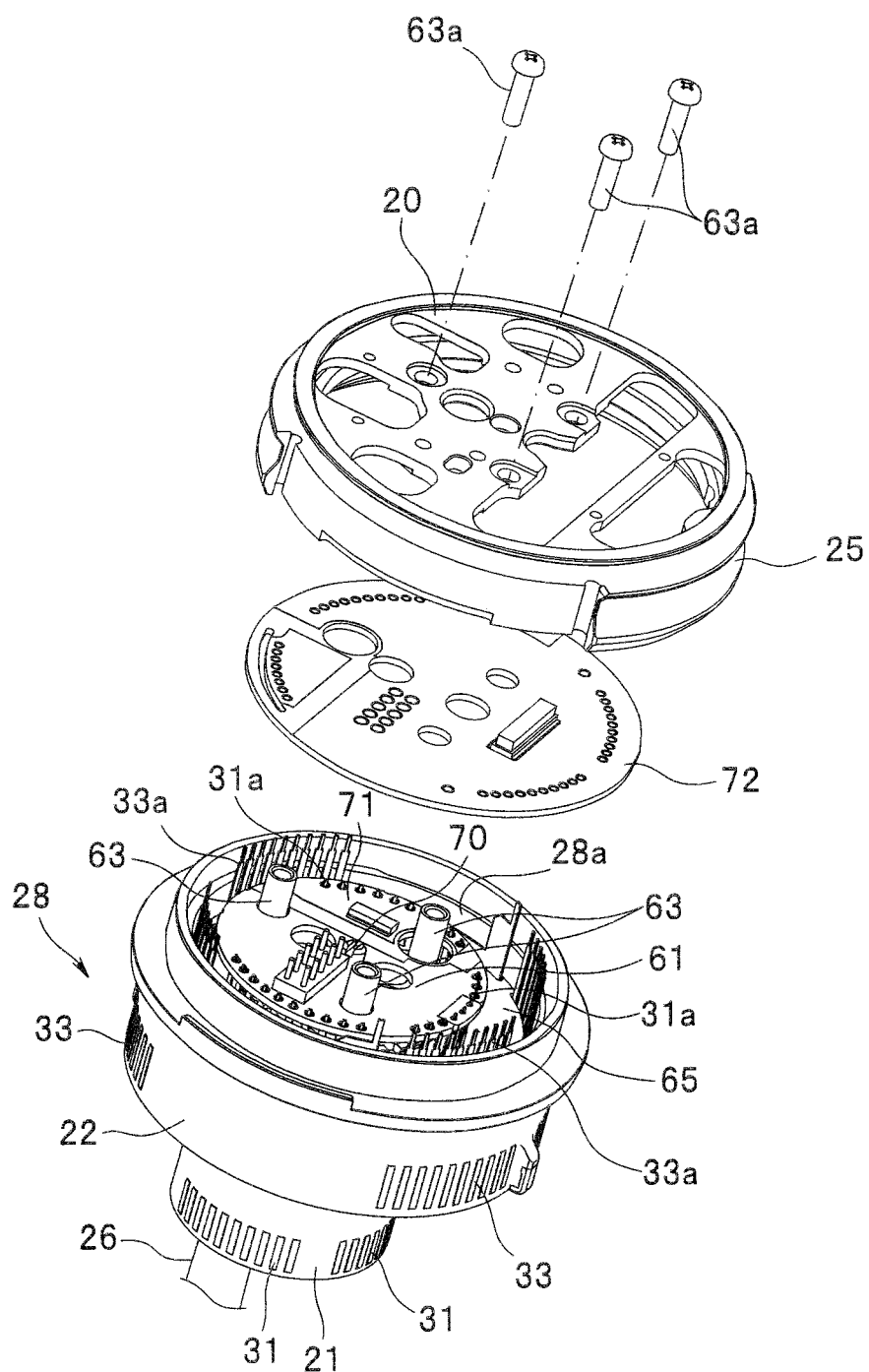
FIG. 10 relates to the first embodiment of the present invention, and is an exploded perspective view showing a configuration in which a second board and a disk-shaped metal frame are connected to the electric plug portion.
Figure 11:
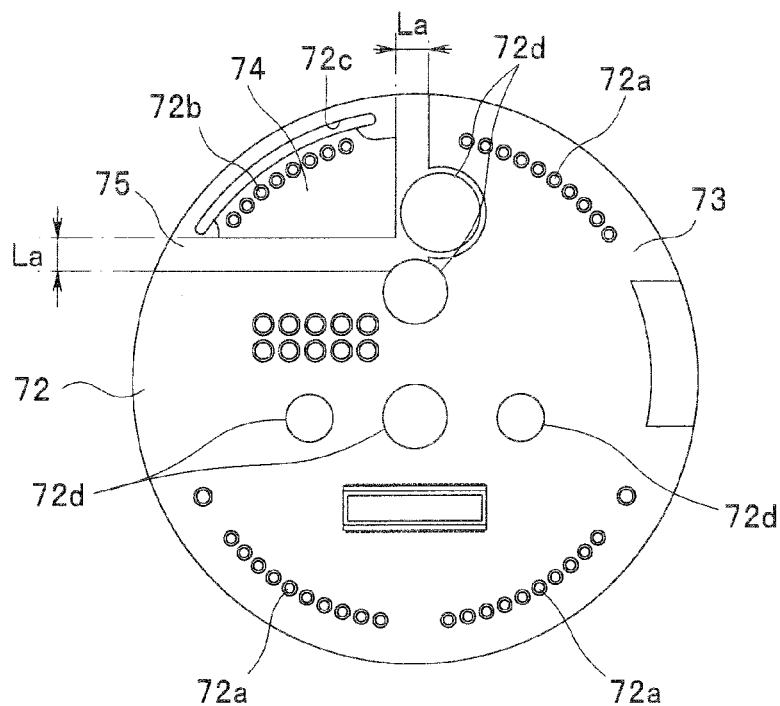
FIG. 11 relates to the first embodiment of the present invention, and is a plane view showing a configuration of the second board.
Figure 12:
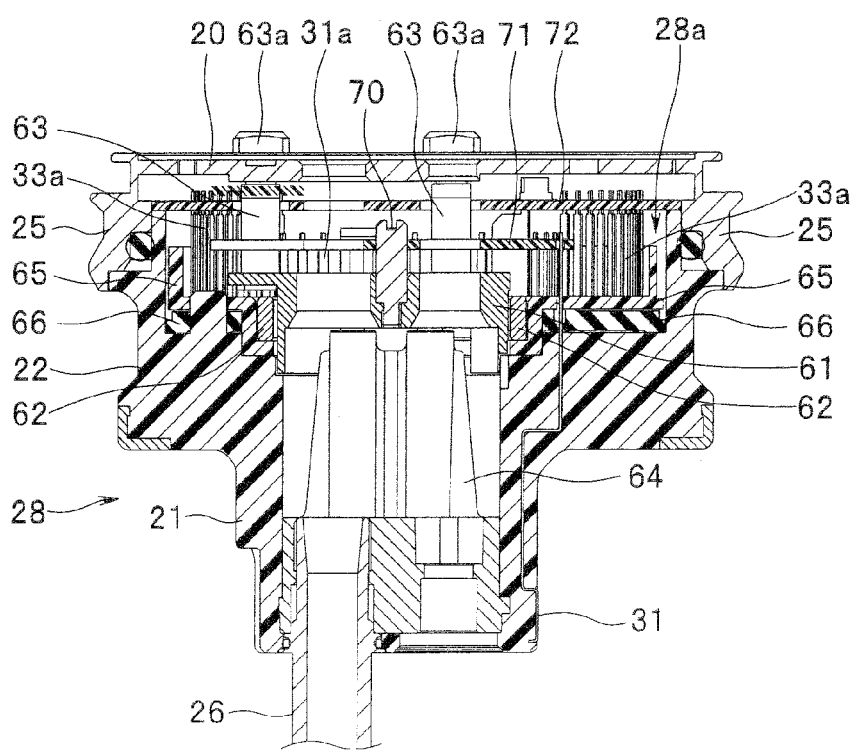
FIG. 12 relates to the first embodiment of the present invention, and is a sectional view showing a configuration of the electric plug portion to which the first and the second boards and the disk-shaped metal frame are fixed.
Figure 13:
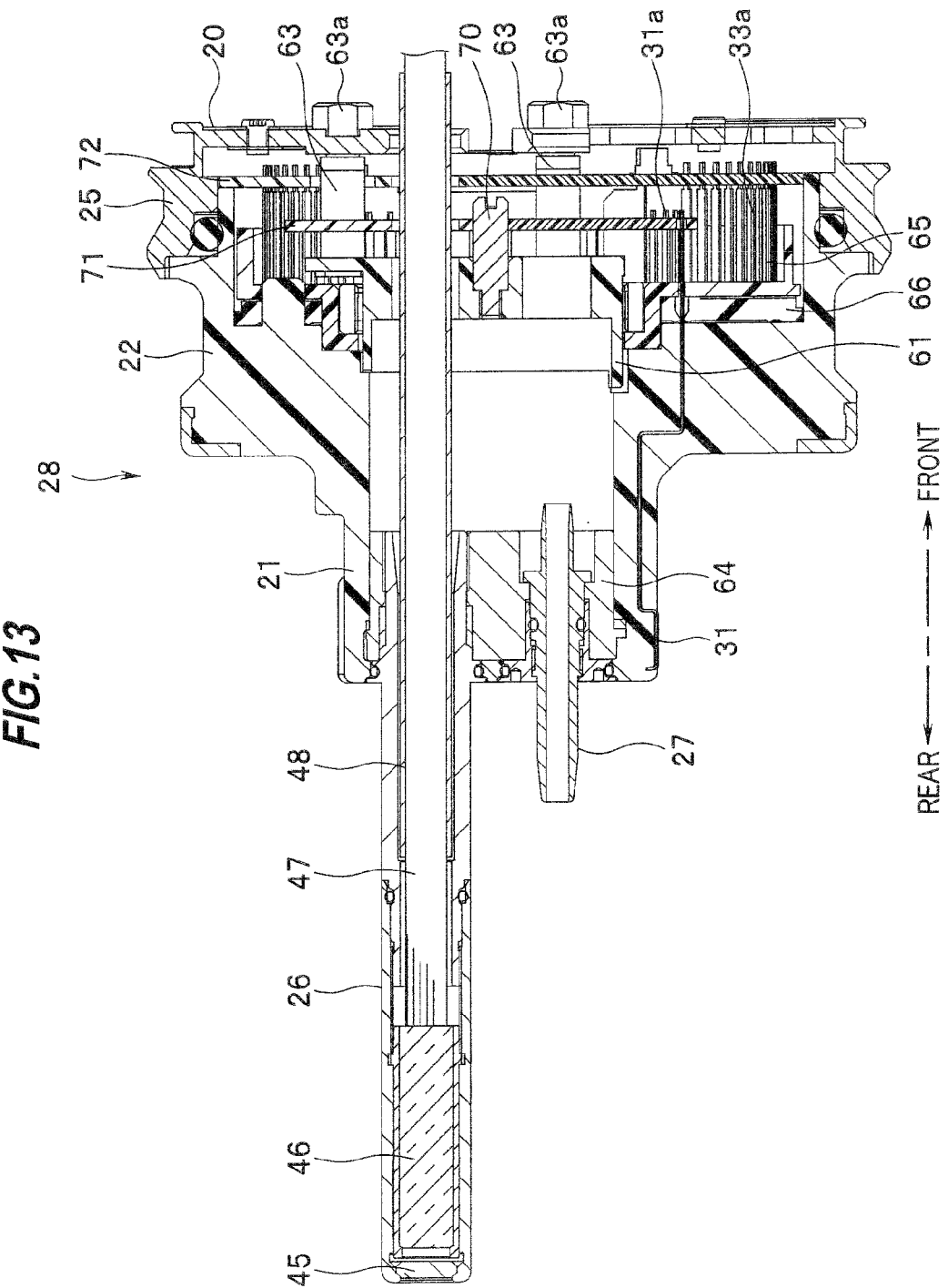
FIG. 13 relates to the first embodiment of the present invention, and is a sectional view showing a configuration of a proximal end portion of the endoscope connector.
Figure 14:
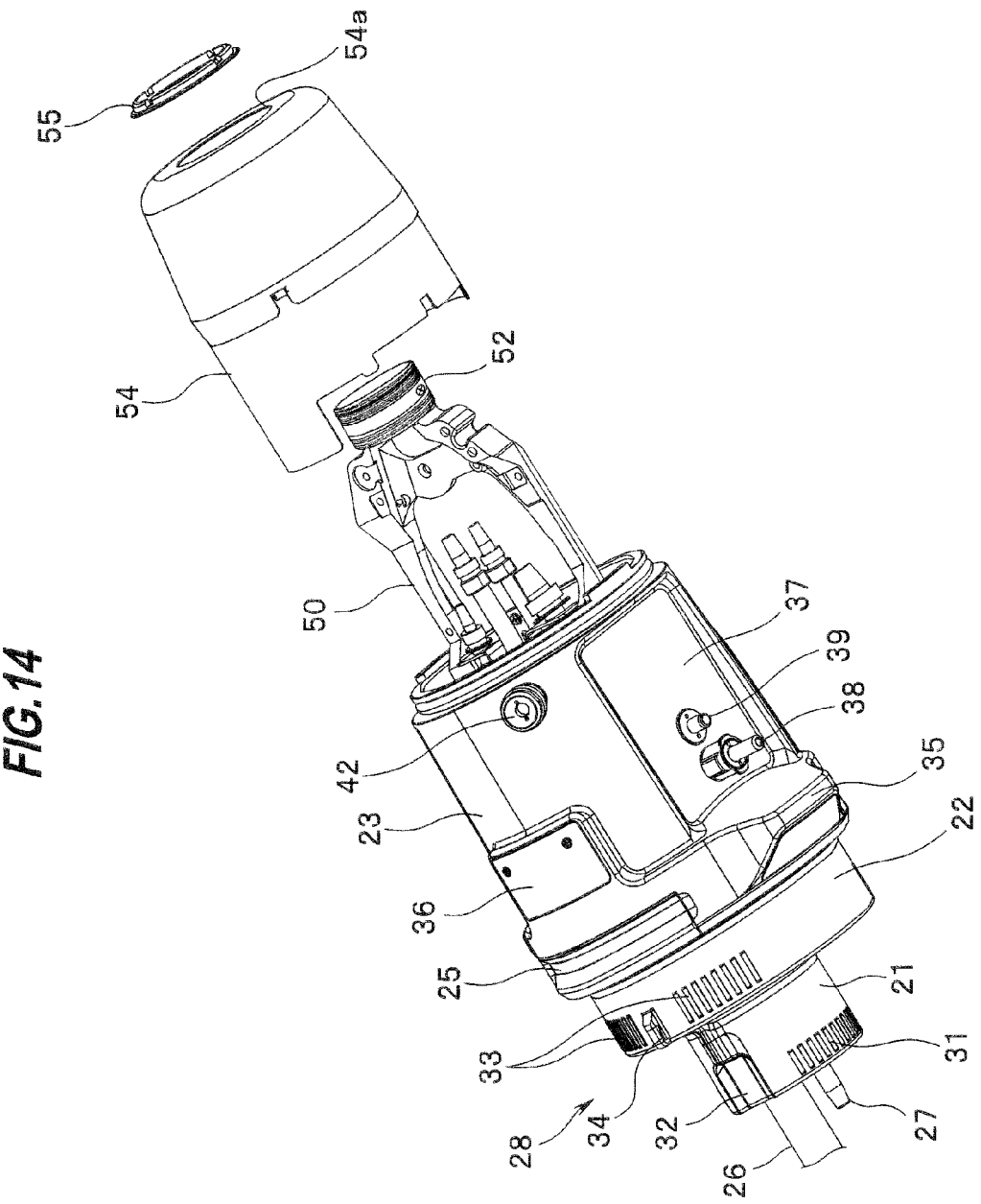
FIG. 14 relates to the first embodiment of the present invention, and is an exploded perspective view showing a configuration in which a shield member is fitted to the connector provided with a connector case.
Figure 15:
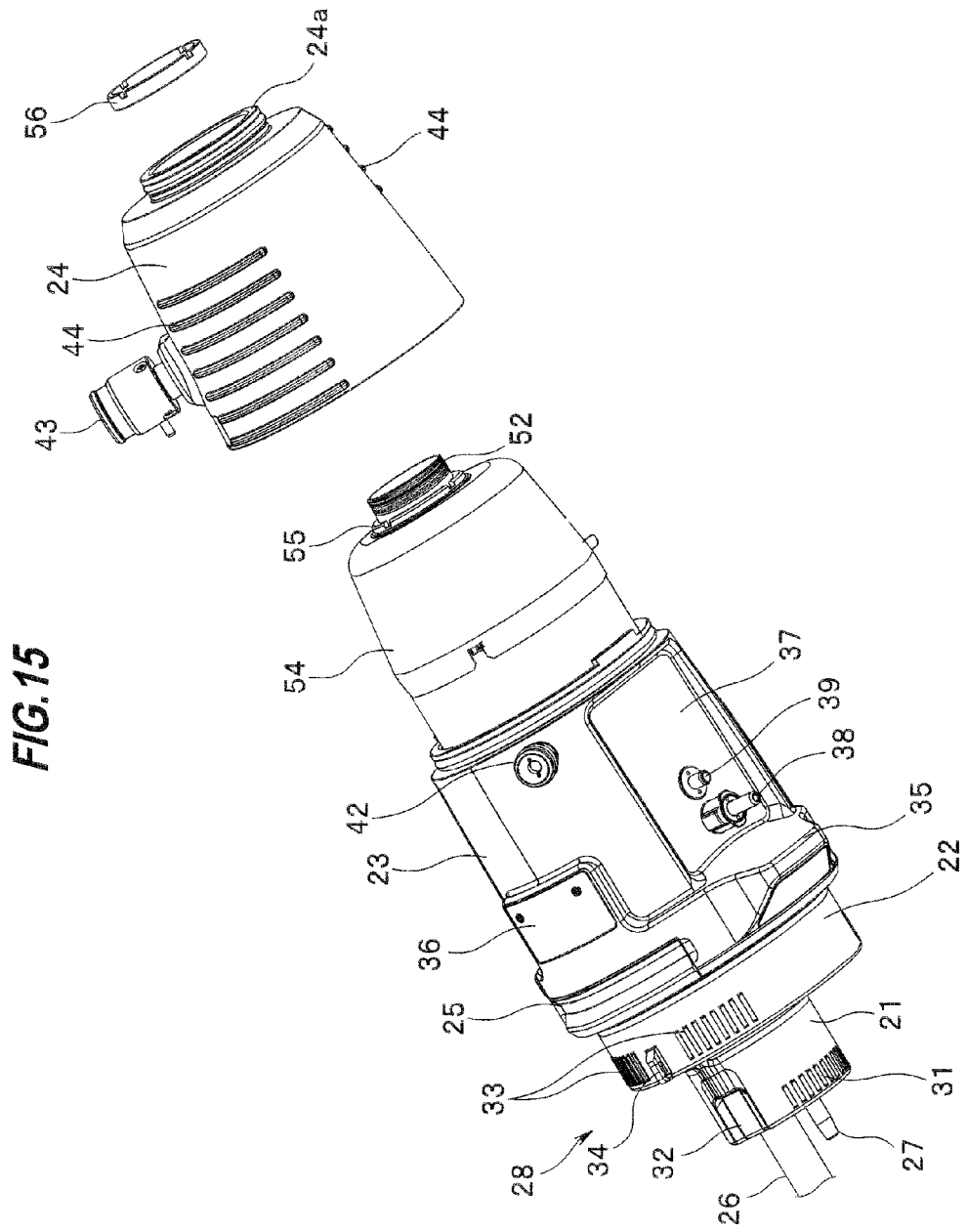
FIG. 15 relates to the first embodiment of the present invention, and is an exploded perspective view showing a configuration in which a connector cover covering the shield member is fitted to the endoscope connector from FIG. 14.
Figure 16:
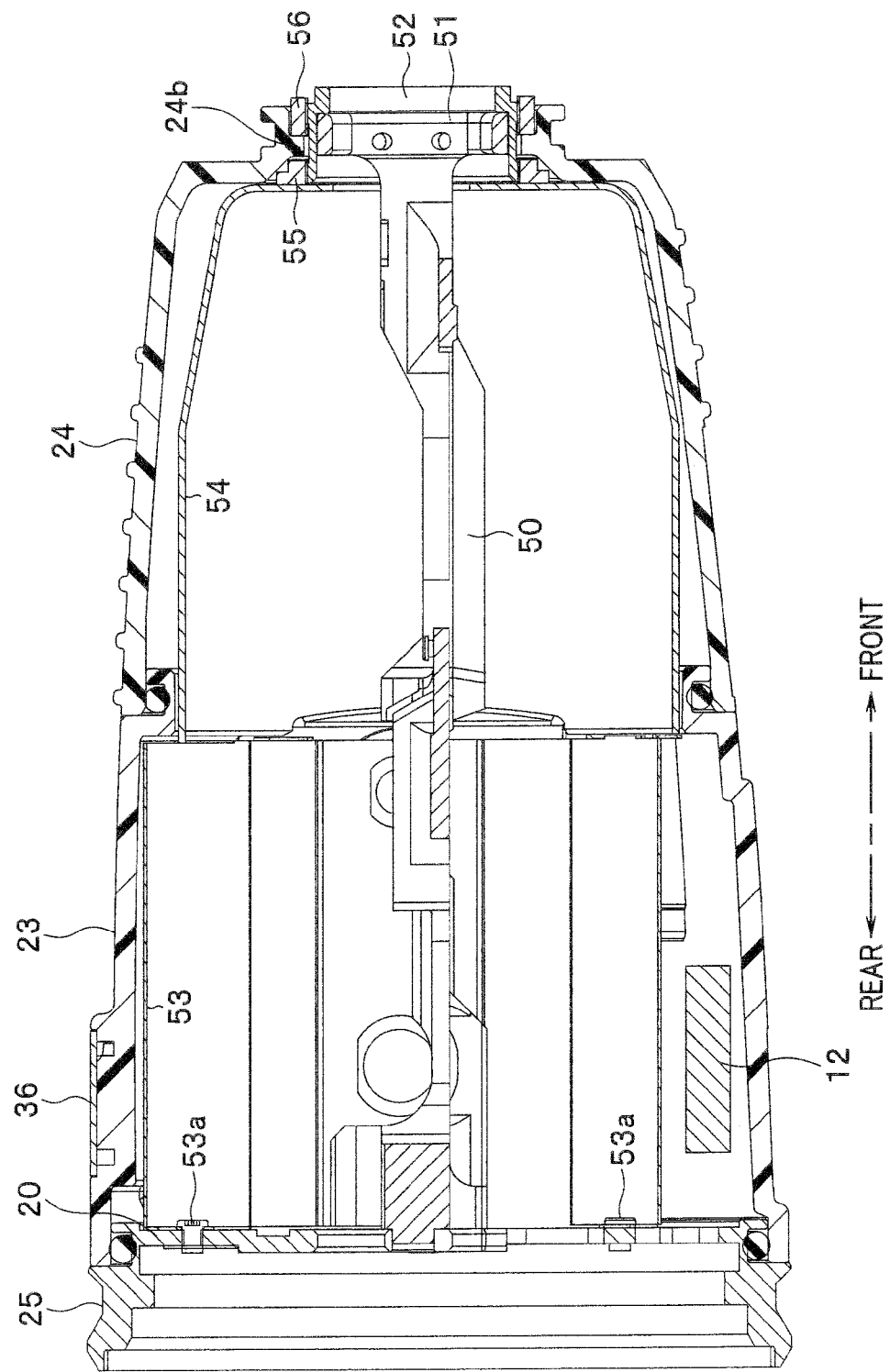
FIG. 16 relates to the first embodiment of the present invention, and is a sectional view showing a configuration of a distal end portion of the endoscope connector.
Figure 17:
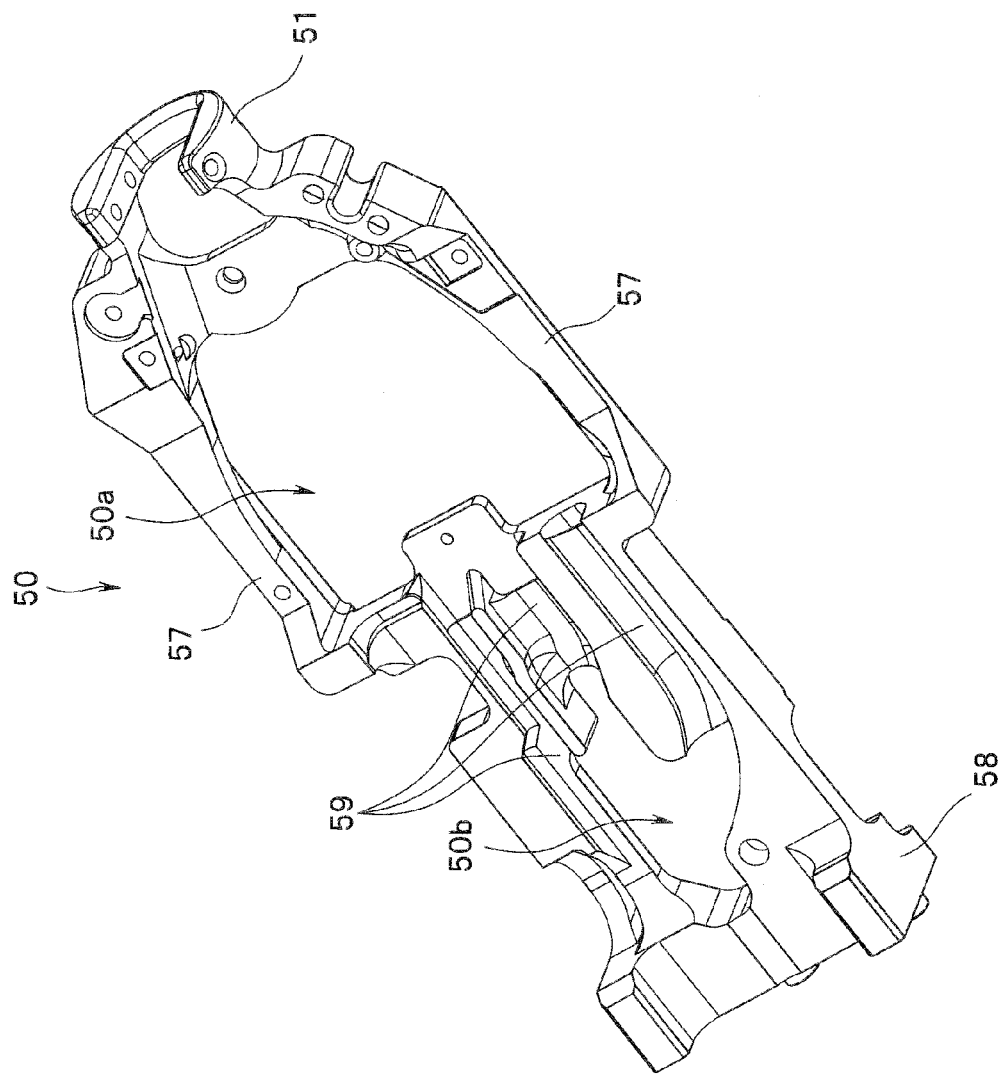
FIG. 17 relates to the first embodiment of the present invention, and is a perspective view showing a configuration of a main frame member.
Figure 18:
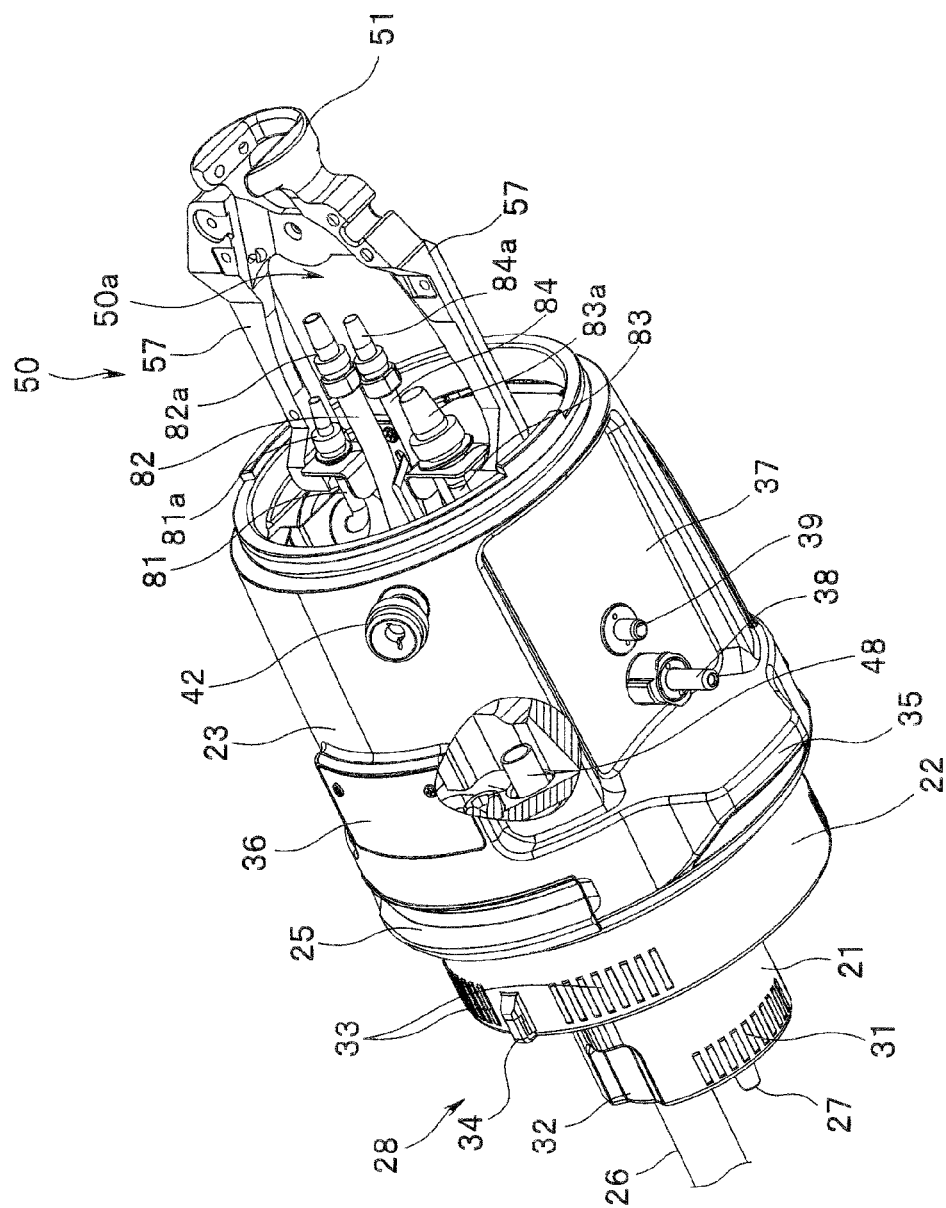
FIG. 18 relates to the first embodiment of the present invention, and is a perspective view of the endoscope connector showing a state in which various conduits are disposed in the main frame member.
Figure 19:
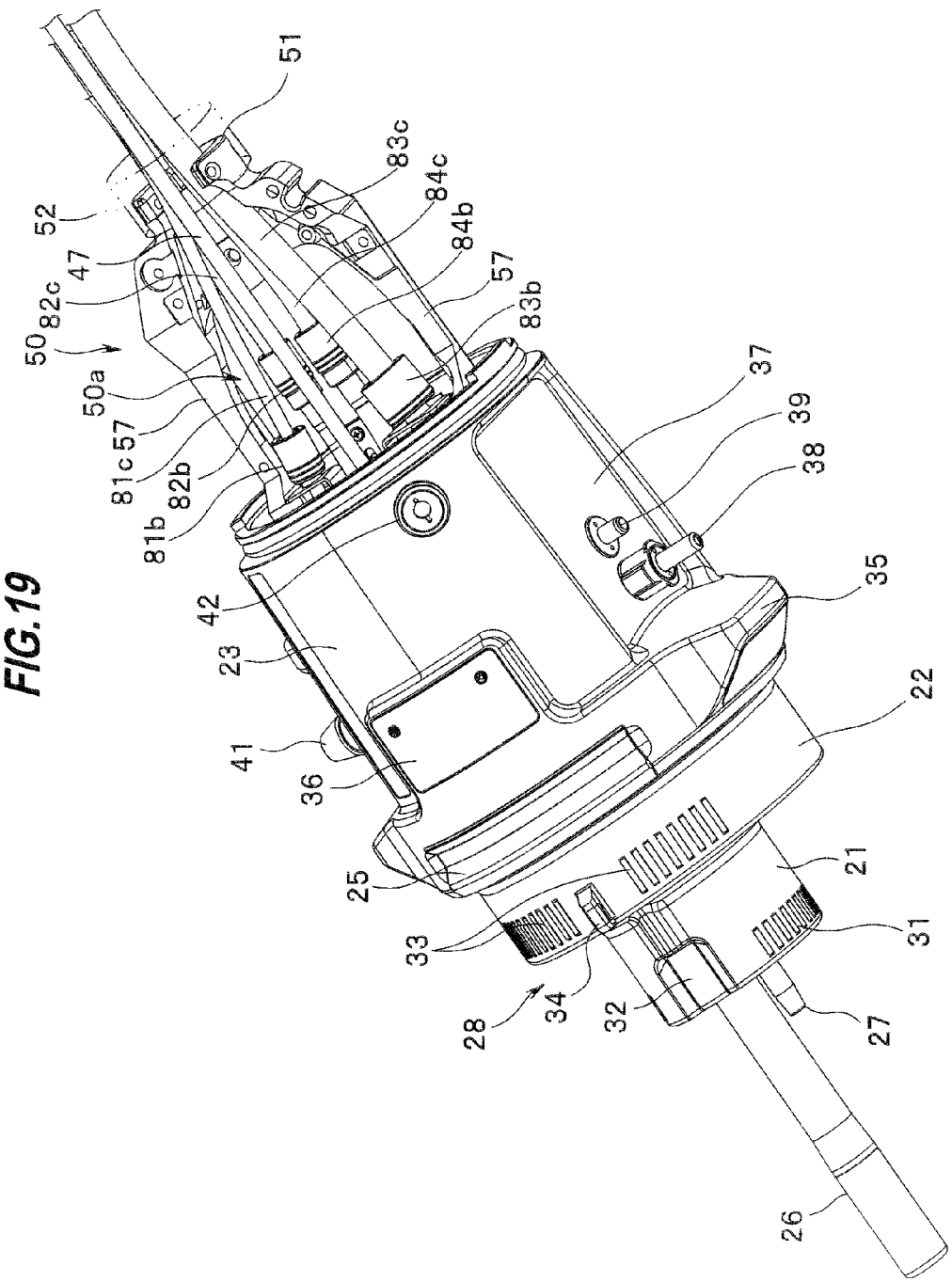
FIG. 19 relates to the first embodiment of the present invention, and is a perspective view of the endoscope connector showing an inside in a state in which various tubes and the like are disposed in the main frame member.
Figure 20:
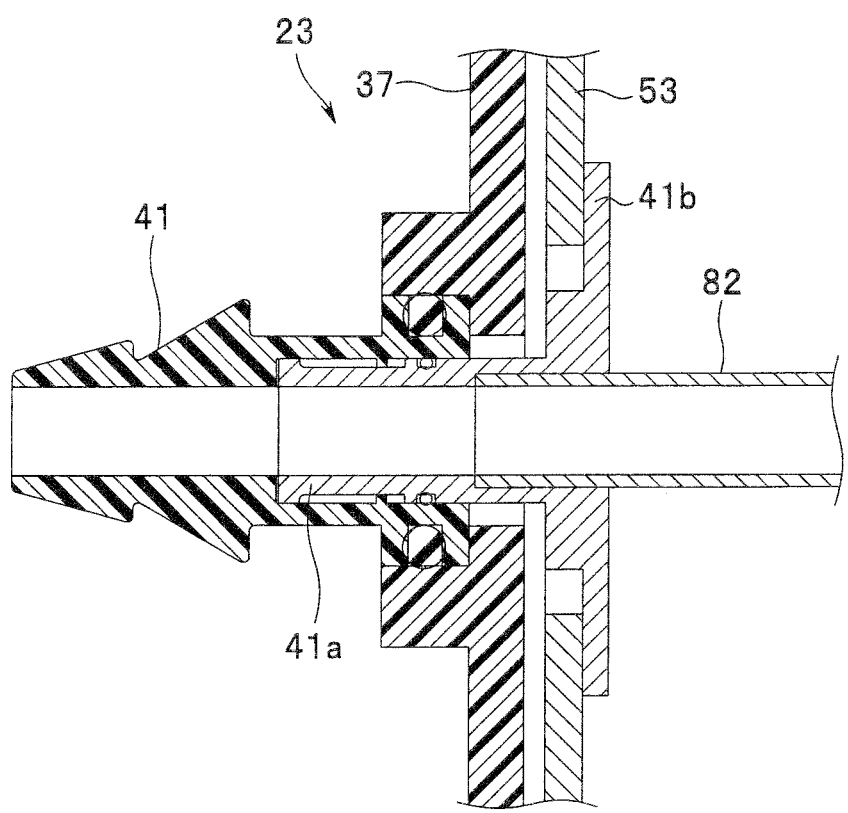
FIG. 20 relates to the first embodiment of the present invention, and is a sectional view showing a configuration of a suction pipe sleeve placed in the connector case.
Figure 21:
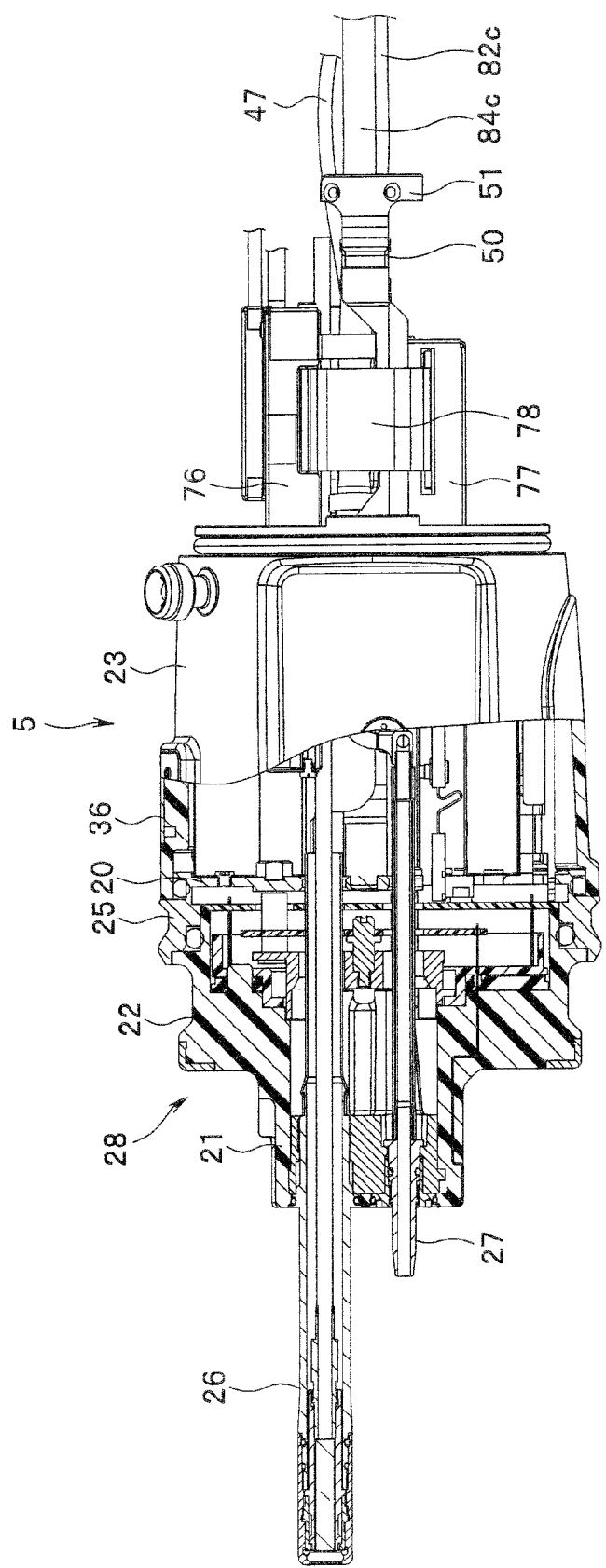
FIG. 21 relates to the first embodiment of the present invention, and is a partial cross-sectional view of the endoscope connector showing a state in which shield cases are placed at both surface sides of the main frame member.
Figure 22:
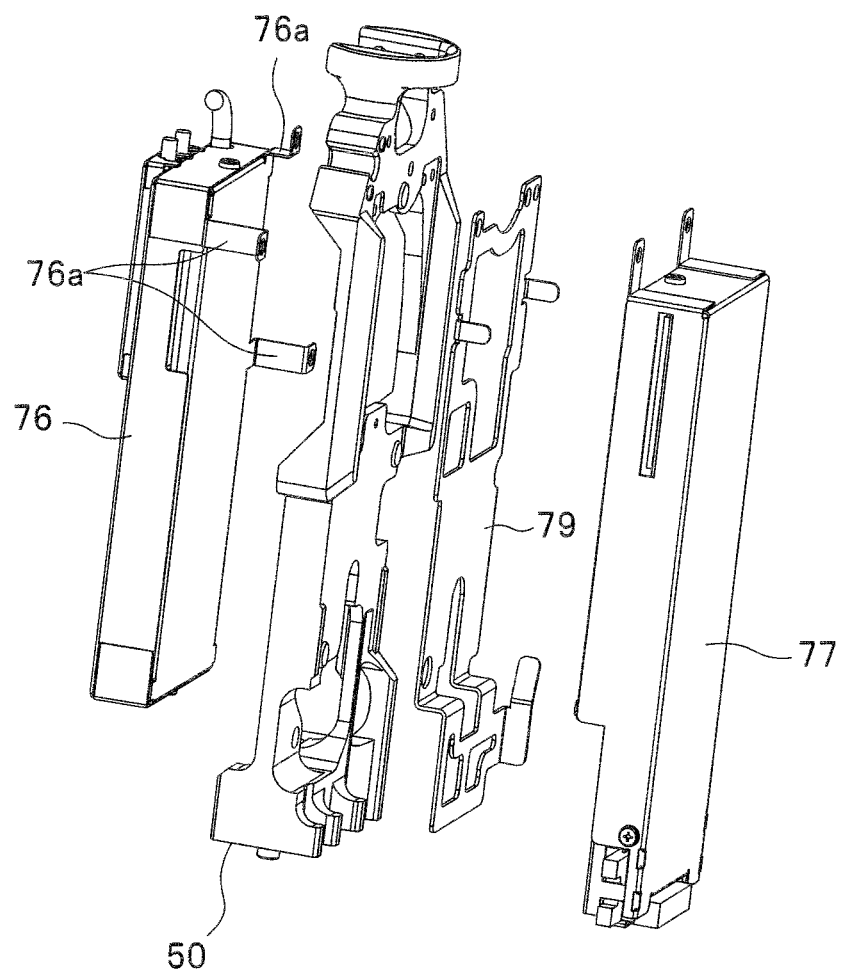
FIG. 22 relates to the first embodiment of the present invention, and is an exploded perspective view showing configurations of two shield cases placed at both the surface sides of the main frame member and a board base.
Figure 23:
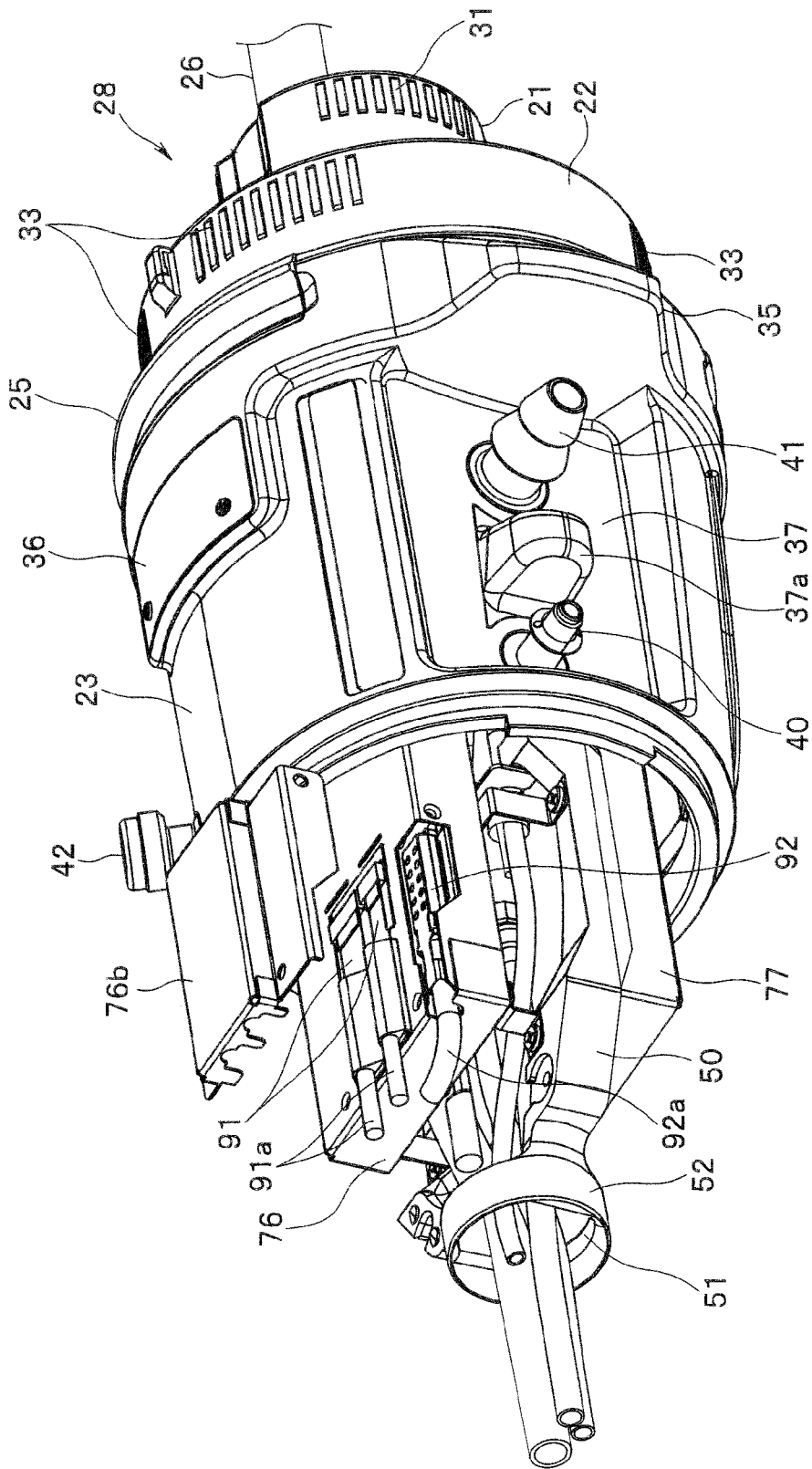
FIG. 23 relates to the first embodiment of the present invention, and is a perspective view of the endoscope connector showing a state in which the two shield cases are placed at both the surface sides of the main frame member.
Figure 24:
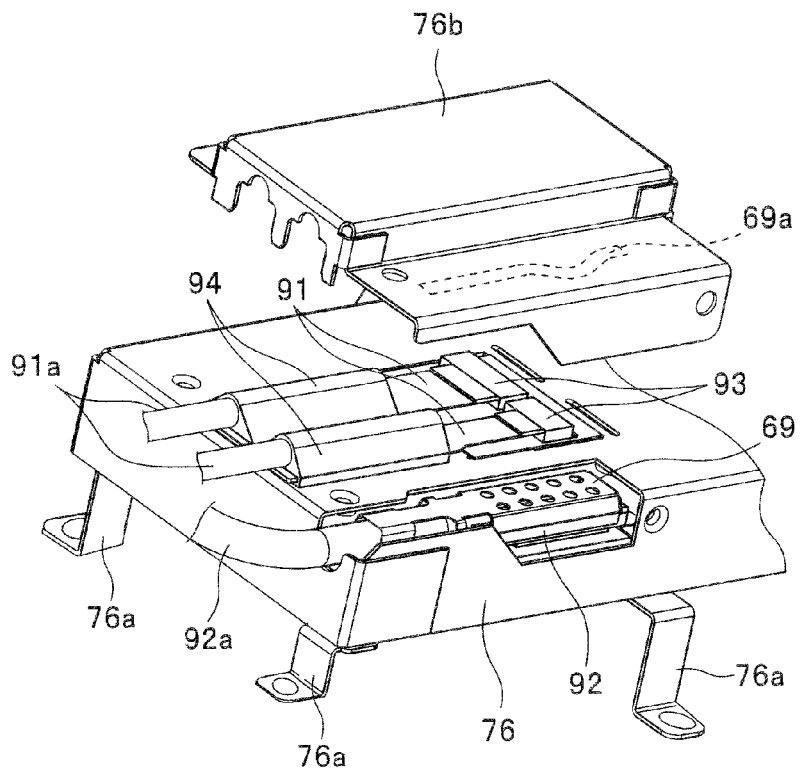
FIG. 24 relates to the first embodiment of the present invention, and is a perspective view showing an electric wiring configuration of a first shield case.
Figure 25:
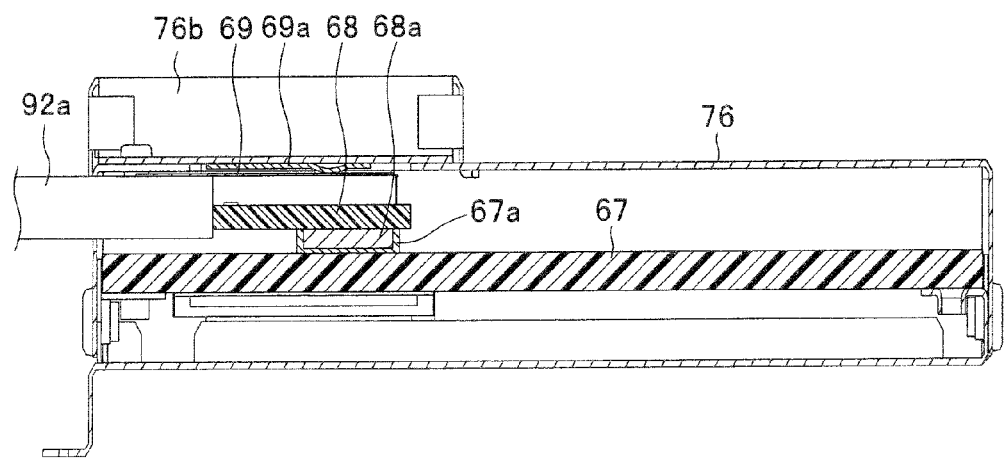
FIG. 25 relates to the first embodiment of the present invention, and is a sectional view showing a configuration of the first shield case.
Figure 26:
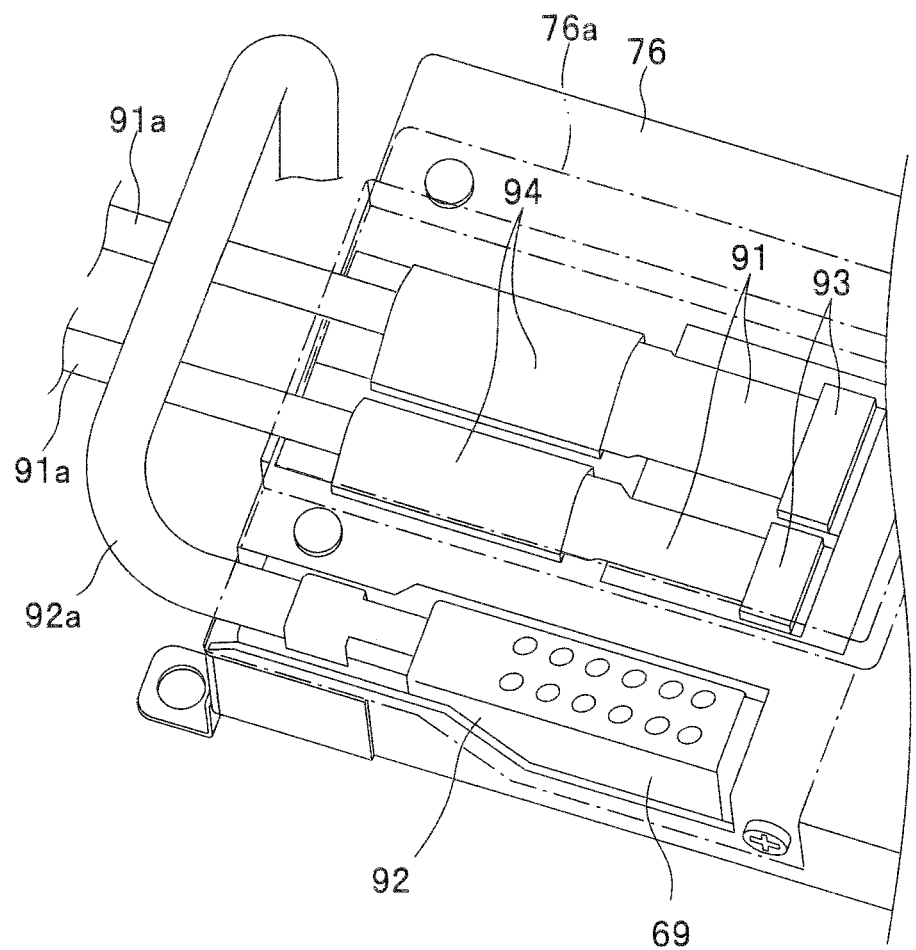
FIG. 26 relates to the first embodiment of the present invention, and is a perspective view showing the electric wiring configuration of the first shield case by enlarging the electric wiring configuration.
Figure 27:
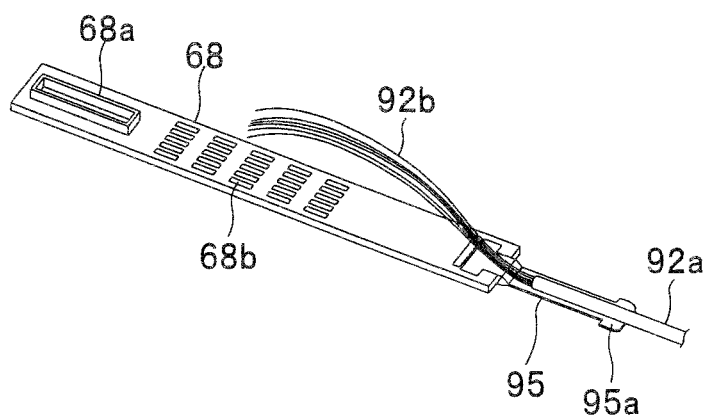
FIG. 27 relates to the first embodiment of the present invention, and is a perspective view showing a cable wiring configuration of a connector board.
Figure 28:
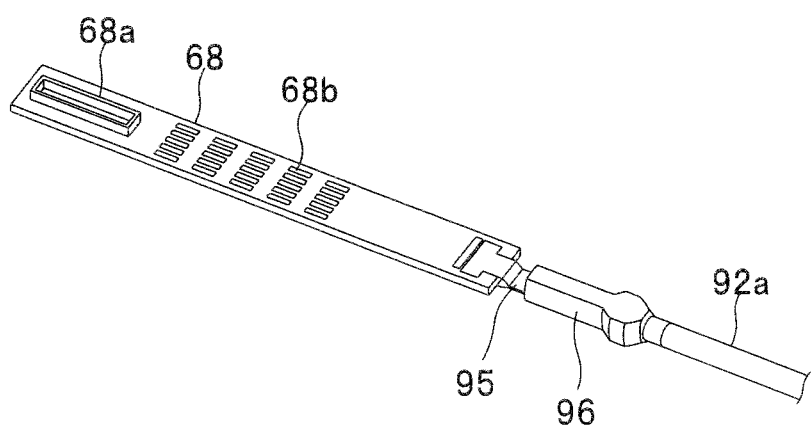
FIG. 28 relates to the first embodiment of the present invention, and is a perspective view showing a configuration of the connector board after cable wiring.
Figure 29:
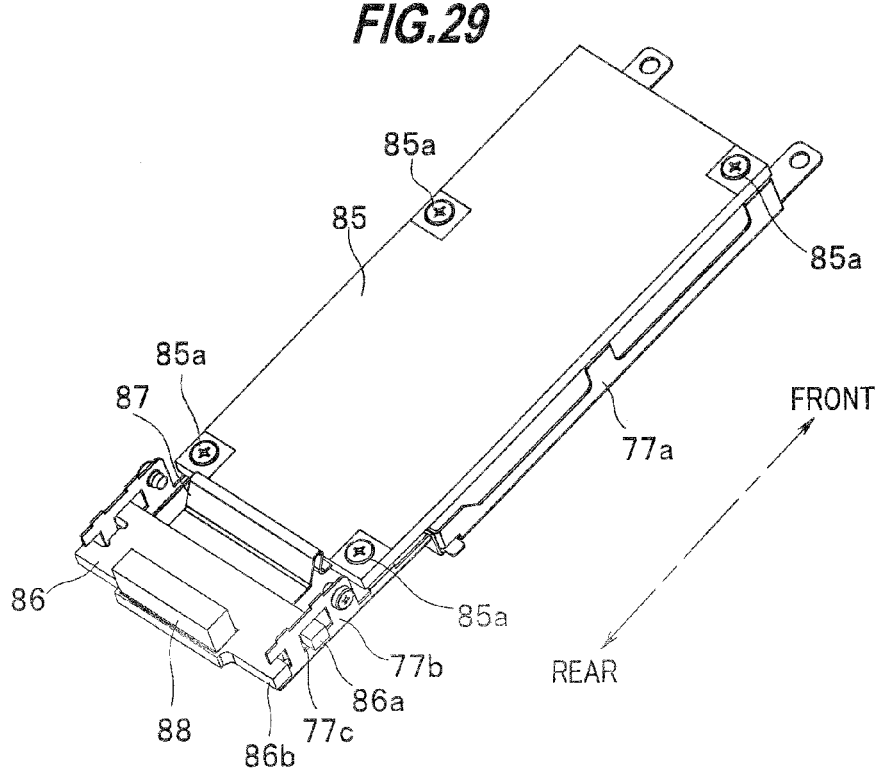
FIG. 29 relates to the first embodiment of the present invention, and is a perspective view showing a configuration of an electric board placed in a second shield case.
Figure 30:
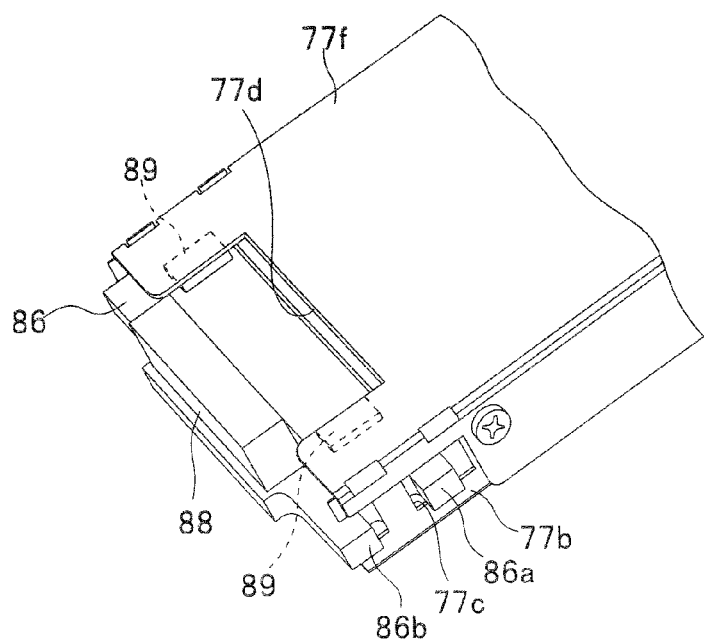
FIG. 30 relates to the first embodiment of the present invention, and is a perspective view showing a connector configuration of the electric board.
Figure 31:
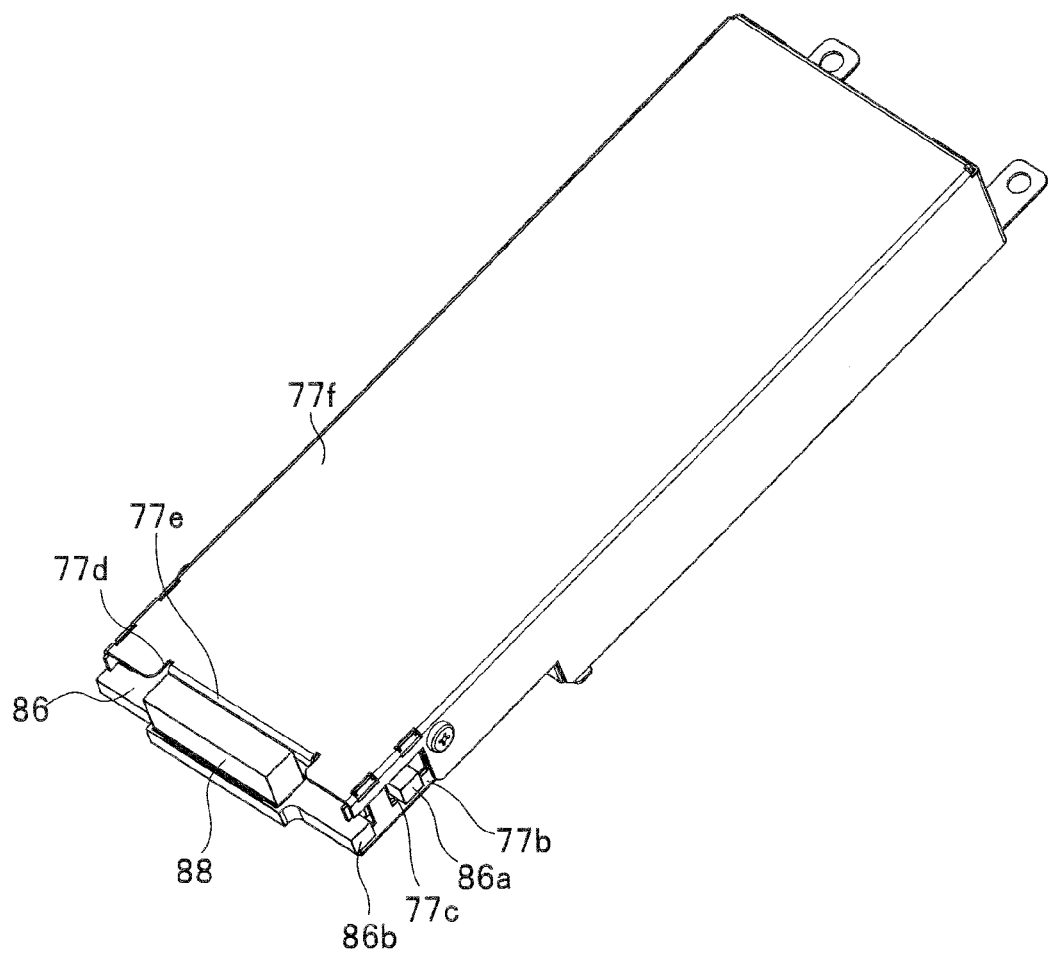
FIG. 31 relates to the first embodiment of the present invention, and is a perspective view showing a second shield case and a connector configuration of an electric board of a modified example.
Figure 32:
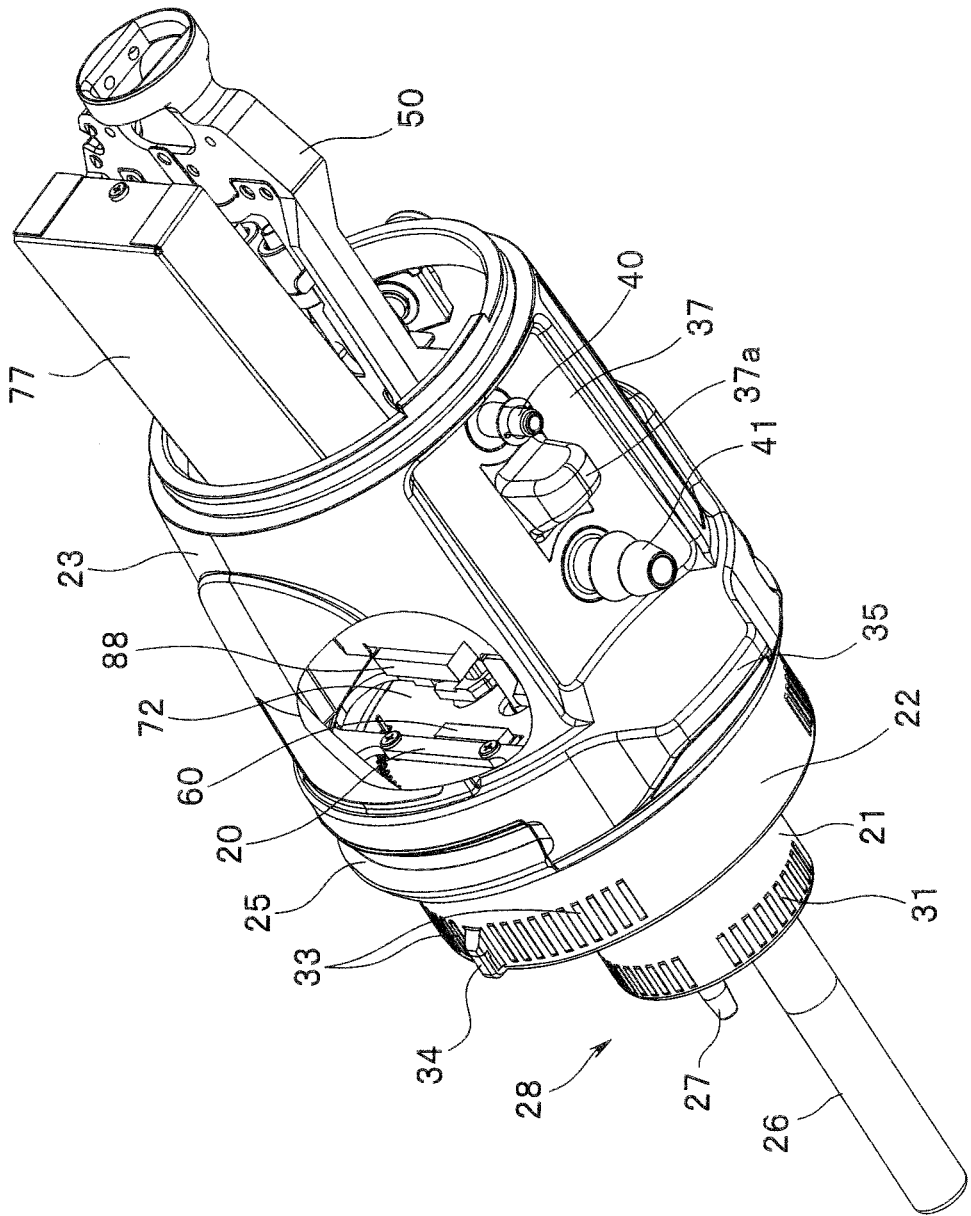
FIG. 32 relates to the first embodiment of the present invention, and is a perspective view of the endoscope connector showing a state in which the connector of the electric board in the second shield case is connected to a connector of a second board placed in the electric plug portion.

Further, FIGS. 1 to 32 relate to the present invention. FIG. 1 is a perspective view showing an entire configuration of the endoscope apparatus. FIG. 2 is a perspective view showing a configuration of an endoscope connector. FIG. 3 is a perspective view showing the configuration of the endoscope connecter at an angle different from FIG. 2. FIG. 4 is a perspective view showing the configuration of the endoscope connecter seen from a front side. FIG. 5 is a partial cross-sectional view showing the configuration of the endoscope connector connected to an external device. FIG. 6 is a sectional view showing the configuration of the endoscope connector. FIG. 7 is an exploded perspective view showing a configuration in which a support plate is fixed to an electric plug portion. FIG. 8 is a sectional view showing a configuration of the electric plug portion to which the support plate is fixed. FIG. 9 is an exploded perspective view showing a configuration in which a first board is connected to the electric plug portion. FIG. 10 is an exploded perspective view showing a configuration in which a second board and a disk-shaped metal frame are connected to the electric plug portion. FIG. 11 is a plane view showing a configuration of the second board. FIG. 12 is a sectional view showing a configuration of the electric plug portion to which the first and the second boards and the disk-shaped metal frame are fixed. FIG. 13 is a sectional view showing a configuration of a proximal end portion of the endoscope connector. FIG. 14 is an exploded perspective view showing a configuration in which a shield member is fitted to the connector provided with a connector case. FIG. 15 is an exploded perspective view showing a configuration in which a connector cover covering the shield member is fitted to the endoscope connector from FIG. 14. FIG. 16 is a sectional view showing a configuration of a distal end portion of the endoscope connector. FIG. 17 is a perspective view showing a configuration of a main frame member. FIG. 18 is a perspective view of the endoscope connector showing a state in which various conduits are disposed in the main frame member. FIG. 19 is a perspective view of the endoscope connector showing an inside in a state in which various tubes and the like are disposed in a main frame member. FIG. 20 is a sectional view showing a configuration of a suction pipe sleeve placed in the connector case. FIG. 21 is a partial cross-sectional view of the endoscope connector showing a state in which shield cases are placed at both surface sides of the main frame member. FIG. 22 is an exploded perspective view showing configurations of two shield cases placed at both surface sides of the main frame member and a board base. FIG. 23 is a perspective view of the endoscope connector showing a state in which the two shield cases are placed at both the surface sides of the main frame member. FIG. 24 is a perspective view showing an electric wiring configuration of a first shield case. FIG. 25 is a sectional view showing a configuration of the first shield case. FIG. 26 is a perspective view showing the electric wiring configuration of the first shield case by enlarging the electric wiring configuration. FIG. 27 is a perspective view showing a cable wiring configuration of a connector board. FIG. 28 is a perspective view showing a configuration of the connector board after cable wiring. FIG. 29 is a perspective view showing a configuration of an electric board placed in a second shield case. FIG. 30 is a perspective view showing a connector configuration of the electric board. FIG. 31 is a perspective view showing a second shield case and a connector configuration of an electric board of a modified example. FIG. 32 is a perspective view of the endoscope connector showing a state in which the connector of the electric board in the second shield case is connected to a connector of a second board placed in the electric plug portion.

First, an endoscope apparatus 1 has an insertion portion 2 as an elongated long member which is inserted into a site to be observed, in this case, a lumen of a large intestine or the like, an operation section 3 which is connectively provided at a proximal end portion of the insertion portion 2, a universal cable 4 which is a composite cable provided extensively from a side surface of the operation section 3, and an endoscope connector (hereinafter, abbreviated simply as a connector) 5 which is provided at an end portion of the universal cable 4 and is a connector for a medical instrument detachably connected to an external device which is a video processor (not illustrated) integrated with a light source apparatus, as shown in FIG. 1.

The insertion portion 2 of the endoscope apparatus 1 has, at a distal end side, a distal end portion 6 in which image pickup means is contained, and a bending portion 7 as a bendable moving section is connected to a rear portion of the distal end portion 6. Furthermore, a flexible tube portion 8 which is formed of a soft tubular member, is long and has flexibility is connectively provided at a rear portion of the bending portion 7. The flexible tube portion 8 of the insertion portion 2 has a proximal end portion connected to a bend preventing portion 9 of the operation section 3.

The operation section 3 of the endoscope apparatus 1 is provided to be connected to the above described bend preventing portion 9, and includes a grasping portion 10 for a user to grasp at the time of use. A treatment instrument insertion port 11 which configures a proximal end opening of a treatment instrument channel (not illustrated) which is placed in the insertion portion 2 is provided in a connectively provided portion of the bend preventing portion 9 and the grasping portion 10. Further, a bending operation section 17 having two bending operation knobs 15 in this case which perform bending operation of the bending portion 7 of the insertion portion 2, and a fixing lever 16 for fixing the bending operation knobs 15 at desired turn positions is placed at the grasping portion 10 of the operation section 3. Further, the grasping portion 10 is provided with switches 13 and 14 for operating various endoscope functions.

At the universal cable 4 of the endoscope apparatus 1, bend preventing members 18 and 19 for preventing damage by twist and the like by keeping connection strength are placed in such a manner as to cover outer circumferential portions of both end portions connected to the operation section 3 or the connector 5.

Next, a configuration of the connector 5 included by the endoscope apparatus 1 of the present embodiment will be described below based on FIG. 2 and the following drawings. The connector 5 of the present embodiment is placed at a proximal end of the endoscope apparatus 1 which is a terminal end of the universal cable 4, and therefore, will be described hereinafter with the side which is connected to the universal cable 4 described as a distal end (front) and the side which is connected to an external device described as a proximal end (rear). Further, the connector 5 is connected to an external device placed in an operation room, and therefore, the connector 5 will be described hereinafter with the top, bottom, left and right directions which are specified in the state connected to external device set as the reference.

First, as shown in FIGS. 2 and 3, an outer sheath is formed mainly by an electric plug portion 28 having two electric connector portions 21 and 22 which are formed by being connectively provided in two stages, are in substantially columnar shapes with different outside diameters and integrally formed, a connector case 23 which is a first case body in a substantially cylindrical shape connectively provided at the electric connector portion 22 at the front side, and a connector cover 24 which is a tubular second case body with a diameter tapering to a front toward the bend preventing member 19 and is a grasping portion for a user to grasp mainly with a right hand, in sequence from a proximal end side.

In the two electric connector portions 21 and 22 which belong to the electric plug portion 28, the electric connector portion (hereinafter, sometimes called the first electric connector portion) 21 at the rear side has an outside diameter smaller than the electric connector portion (hereinafter, sometimes called the second electric connector portion) 22 at the front side.

The first electric connector portion 21 is formed to project from an end surface (proximal end surface) of the second electric connector portion 22, and has a plurality of first electric contact points 31 provided side by side along a circumferential direction at a part of a circumferential surface of an outer circumferential portion. Further, in the first electric connector portion 21, a cutout portion 32 for recognizing a scope to which an external device is connected is formed at an edge of the outer circumferential portion of an upper portion side in this case. Furthermore, from an end surface (proximal end surface) of the first electric connector portion 21, a light guide pipe sleeve 26 on which an illuminating light from the external device is incident is extensively provided at an upper portion side, and an air supply pipe sleeve 27 through which gas from the external device is supplied is extensively provided at a lower portion side.

In the second electric connector portion 22, a plurality of second electric contact points 33 are provided side by side along the circumferential direction at a part of the circumferential surface of an outer circumferential portion. Further, two projection portions 34 for rotational positioning at the time of being connected to an external device are provided at a top and a bottom of an edge of the outer circumferential portion in this case.

The connector case 23 includes two pipe sleeve disposition surfaces 37 which are planarly formed at both side portions of a central portion. One of the pipe sleeve disposition surfaces 37 is provided with a water supply pipe sleeve 38 and a pressurized pipe sleeve 39 (see FIG. 2), and the other pipe sleeve disposition surface 37 is provided with a forward water supply pipe sleeve 40, a suction pipe sleeve 41, and a projection portion 37a for protecting the pipe sleeves 40 and 41 (see FIG. 3). Further, the connector case 23 has pipe sleeve protection projected portions 35 which project in both left and right directions from the edge of the outer circumferential side portion of the end portion (proximal end portion) to protect the water supply pipe sleeve 38, the pressurized pipe sleeve 39, the forward water supply pipe sleeve 40 and the suction pipe sleeve 41.

Further, in the connector case 23, a nameplate 36 for displaying a manufacturer, a model, a date of manufacture, use and the like is provided at an intermediate portion of the upper portion side of the outer circumferential portion, and an earth terminal 42 is provided at a front portion of the upper portion side. The connector case 23 has an outer circumferential edge cut out at two upper and lower spots of the end portion (proximal end portion), and a flange portion 25 of a disk-shaped metal frame is exposed from the cutout portions. The disk-shaped metal frame will be described in detail later.

The connector cover 24 is provided with a water leakage detection pipe sleeve 43 at an intermediate portion of a side portion of an outer circumferential portion. The water leakage detection pipe sleeve 43 is placed at a position having a predetermined angle θ, an angle of approximately 50° in this case, in a diagonally right direction with respect to the vertical direction of the connector 5 in a state in which the connector is faced to a rear side (proximal end side) as shown in FIG. 4. Further, a plurality of anti-skid projected portions 44 are formed at a part of a top and a part of a bottom of the outer circumferential portion.

The connector 5 has the placing position of the water leakage detection pipe sleeve 43, which projects from the connector cover 24, provided at a position inclined by approximately 50° (angle θ=substantially 50°) in the diagonally right direction with respect to the vertical direction as above, whereby when the user makes access to the connector from the upper portion direction, and grasps the connector cover 24 portion with the right hand, the water leakage detection pipe sleeve 43 is located between an index finger and a thumb. Consequently, the water leakage detection pipe sleeve 43 does not interfere with the right hand, and therefore, does not become an obstacle, and thus, the user can naturally grasp the connector cover 24 portion of the connector 5.

Thereby, the connector 5 is configured to be easily handled without impairment of graspability. The vertical direction of the connector 5 is the vertical direction in the state in which the connector 5 is connected to an external device as described above. In this case, the nameplate 36 which is provided on the connector case 23 is on the upper portion side, and the nameplate 36 serves as an indicator showing the upper portion of the connector 5.

Further, the connector 5 has an RFID chip 12 placed in a lower position in the connector case 23 (see FIG. 5). The RFID chip 12 stores various kinds of information such as type information of the endoscope apparatus 1. A projected portion 23a is provided on an outer circumferential lower portion surface of the connector case 23 so that a user can easily recognize the installation location of the RFID chip 12. Besides, as the other scheme to enhance recognition of the user, the installation location of the RFID chip 12 in the outer circumferential surface of the connector case 23 may be planarly formed.

The connector 5 is configured to be provided with the RFID chip 12 in the lower portion as above, whereby the advantages is provided, that when the endoscope apparatus 1 is set in a cleaning tank of a cleaning and sterilizing apparatus which is used for cleaning and sterilizing before and after use, the information of the RFID chip 12 provided in the connector 5 can be reliably and automatically read with an antenna provided at the apparatus inner portion side corresponding to the position of the cleaning tank.

More specifically, in order that the cleaning and sterilizing apparatus reliably and automatically reads the information of the RFID chip 12, a distance between the RFID chip 12 and the antenna has to be within a specific range when the endoscope apparatus 1 is set in the cleaning tank. Therefore, a set form of the endoscope apparatus 1 in the cleaning tank of the cleaning and sterilizing apparatus needs to be specified minutely, which becomes a burden on the user, and therefore, even in a state in which the endoscope apparatus 1 is casually set in the cleaning tank, the distance between the RFID chip 12 and the antenna is desirably stabilized.

In the endoscope apparatus 1, the orientation of the connector 5 is specified. More specifically, in the connector 5, the upper portion is oriented in a direction vertically upward when the universal cable 4 is extended in a state in which the operation section 3 of the endoscope apparatus 1 is placed in such a manner that each of the bending operation knobs 15 faces vertically upward. As for the upper portion direction in the connector 5, the nameplate 36 provided on the connector case 23 is on the upper portion side as described above. More specifically, the RFID chip 12 is placed in the outer circumferential portion of the connector case 23 on the side opposite from the nameplate 36 (the lower position rotated by 180° around the outer circumference of the connector case 23 with respect to the nameplate 36 located at the upper position).

The antenna which reads the information of the RFID chip 12 can be provided in an optional position of a bottom surface of the cleaning tank of the cleaning and sterilizing apparatus, and therefore, even when the endoscope apparatus 1 is casually set in the cleaning tank, the lower portion side of the connector 5 is in contact with the bottom surface of the cleaning tank. Therefore, the distance between the RFID chip 12 and the antenna is stabilized, and the information can be reliably and automatically read with the antenna.

The connector 5 may be provided with the RFID chip 12 at the upper portion side without being limited to the aforementioned configuration. In the case of the configuration, if the antenna is provided at a lid portion with which the cleaning tank of the cleaning and sterilizing apparatus is covered, the effect which is equivalent to the aforementioned effect can be obtained. Furthermore, in the connector 5, the RFID chip 12 is provided at the upper portion side, whereby the installation location of the RFID chip 12 easily catches the eye of the user, and the advantage is provided, that the installation location of the RFID chip 12 is easily recognized by the user.

As above, when the endoscope apparatus 1 is set in the cleaning and sterilizing apparatus, the distance between the RFID chip 12 provided in the connector 5, and the antenna which reads the information thereof and is provided at the cleaning and sterilizing apparatus is easily stabilized, and various kinds of information such as endoscope information are easily read.

The connector 5 which is configured as above is connected to a connector connection portion 110 of an external device 100 as shown in FIG. 5. In the connecting state to the external device 100, the connector 5 is inserted through a hole portion 105 formed in a casing 101 of the external device 100 to be fitted and disposed in the hole portion 105.

In the connector connection portion 110 of the external device 100, metal fitting portions 102 are placed at an upper and a lower portions of the hole portion 105 in an outer surface side of the casing 101. The flange portion 25 of the connector 5 is fitted in and fixed to the fitting portions 102. The flange portion 25 and the fitting portions 102 made of metal are fitted to each other and in contact with each other, whereby grounds of the endoscope apparatus 1 and the external device 100 are connected.

In the hole portion 105, a plurality of electric contact point terminals 103 and 104 which are in contact with and electrically continuous with the respective electric contact points 31 and 33 of the first electric connector portion 21 and the second electric connector portion 22 are placed. Thereby, the endoscope apparatus 1 and the external device 100 can exchange various signals.

Further, in the state in which the connector 5 is connected to the connector connection portion 110, the light guide pipe sleeve 26 is inserted through and held by a holder 106 for positioning an illumination optical system. At this time, an illuminating light transmitted from an illuminating light source such as a halogen lamp in the external device 100 is brought into a state in which the illuminating light can be guided into the endoscope apparatus 1 through the light guide pipe sleeve 26.

Though not illustrated, in the state in which the connector 5 is connected to the connector connection portion 110, a conduit which communicates with air supply means is airtightly connected to the air supply pipe sleeve 27 so that gas from the air supply means such as a bomb and a compressor in the external device 100 can be supplied into the endoscope apparatus 1.

Incidentally, the connector 5 of the present embodiment has the flange portion 25 described above between the second electric connector portion 22 and the connector case 23 so that the flange portion 25 is butted to the second electric connector portion 22 and the connector case 23 from different directions, and the disk-shaped metal frame 20 configuring a sub frame is provided to be sandwiched therebetween. The connector 5 has two portions divided, that are a proximal end portion which is a rear side (A in the drawing) to be the second electric connector portion 22 side, and a distal end portion which is a front side (B in the drawing) to be the connector case 23 side with the disk-shaped metal frame 20 as a boundary, and each of the two portions is fixed in a state compressed in a longitudinal axis direction by receiving a pressure generated by being individually butted to the disk-shaped metal frame 20.

First, with use of FIGS. 7 to 13, a configuration of the rear side (A portion of FIG. 6) of the connector 5 will be described in detail hereinafter based on an assembly state of each component. A recessed portion 28a is formed at an end portion of a distal end side of the second electric connector portion 22 of the electric plug portion 28 as shown in FIGS. 7 and 8, and on an end surface of the recessed portion 28a, a plurality of first contact point pins 31a which are electrically continuous with the plurality of first electric contact points 31 provided side by side by being exposed in the circumferential direction on the outer circumferential portion of the first electric connector portion 21, and a plurality of contact point pins 33a which are electrically continuous with the plurality of electric contact points 33 provided side by side by being exposed in the circumferential direction on the outer circumferential portion of the second electric connector portion 22 are implanted to have predetermined lengths. The first contact point pins 31a, and the second contact point pins 33a are embedded in the electric connector portions 21 and 22 in the state in which the first contact point pins and the second contact point pins are insulated from one another respectively.

The plurality of first contact point pins 31a are arranged in an arc shape in an inner circumferential side in an end surface of the second electric connector portion 22. Meanwhile, the plurality of second contact point pins 33a are arranged in an arc shape in an outer circumferential side in the end surface of the second electric connector portion 22. Further, each of the first contact point pins 31a is installed with a smaller amount of extension and a lower height from the end surface of the second electric connector portion 22 than each of the second contact point pins 33a. Contact sections for performing soldering by being passed through an electric board which will be described later, and step portions which abut on the electric board at both sides of the contact sections are formed at extension ends of the first contact point pins 31a and the second contact point pins 33a.

A holding block 64 including an insert metal which internally fixes and holds the light guide pipe sleeve 26 and the air supply pipe sleeve 27 (not illustrated here) is integrally formed by insert in the electric plug portion 28. The holding block 64 is provided with openings of four screw holes 64a on a surface side exposed at the end portion of the second electric connector portion 22.

In the electric plug portion 28, an elastic body in a shape covering a substantially entire bottom surface of the recessed portion 28a, for example, a rubber waterproof packing 66 (see FIG. 8) is disposed in a state in which the respective contact point pins 31a and 33a are inserted therethrough. Thereafter, in the recessed portion 28a of the electric plug portion 28, a substantially disk-shaped packing gland 65 is disposed on the waterproof packing 66 in a state in which the respective contact point pins 31a and 33a are inserted therethrough.

Next, on the packing gland 65, a support plate 61 in a quasi-disk shape into which a presser ring 62 is screwed is fixed to the recessed portion 28a of the electric plug portion 28. The support plate 61 is provided with a screw groove on an outer circumferential portion on the side fitted in the electric plug portion 28, and the presser ring 62 is screwed into the screw groove.

Further, three screw receiving pipes 63 are placed on the support plate 61. The screw receiving pipes 63 have outward flanges at respective end portions, are inserted through hole portions formed in the support plate 61, and are provided in a state in which the outward flanges abut on the end surface, at the presser ring 62 side, of the support plate 61.

After the support plate 61 is fitted in the recessed portion 28a of the electric plug portion 28, the four screws 61a are screwed into the respective screw holes 64a of the holding block 64, and the support plate 61 is fixedly attached to the inside of the recessed portion 28a of the electric plug portion 28. After the support plate 61 is fixed to the recessed portion 28a of the electric plug portion 28, the presser ring 62 which is screwed to the support plate 61 is rotated in a predetermined direction to move to the packing gland 65 side.

More specifically, the presser ring 62 is rotated, and thereby, the position where the presser ring 62 is screwed to the support plate 61 moves to the packing gland 65 side. The moved presser ring 62 abuts on the packing gland 65, and the packing gland 65 is moved in the direction to compress the waterproof packing 66. The waterproof packing 66 is compressed between a bottom surface of the recessed portion 28a of the electric plug portion 28 and the packing gland 65.

As above, the surroundings of the respective contact point pins 31a and 33a which are embedded in the electric plug portion 28 and extend from the same surface which is the bottom surface of the recessed portion 28a are watertightly held by the one waterproof packing 66 which is compressed by the packing gland 65.

More specifically, the connector 5 of the present embodiment is structured such that the ring-shaped presser ring 62 which moves and presses the packing gland 65 which compresses the waterproof packing 66 is provided to be screwed to the support plate 61 which is a frame body, and the waterproof packing 66 is fastened to be compressed to the bottom surface of the recessed portion 28a of the electric plug portion 28.

In contrast with the configuration as above, in the conventional structure, a filling agent or the like is coated on the periphery of the respective contact point pins 31a and 33a which are the electric contacts projected to the inside of the connector 5 to hold the contact point pins 31a and 33a watertightly, but coating variations of the filling material or the like do not provide stable watertightness, and the coating work, curing time and the like of the filling material cause complication of the work, extension of the working time and the like.

However, in the configuration of the connector 5 of the present embodiment, the two kinds of the respective contact point pins 31a and 33a are led out from the same plane of the bottom surface inside the electric plug portion 28 of the connector 5, the one waterproof packing 66 is applied to the bottom surface of the recessed portion 28a from which the respective contact point pins 31a and 33a are led out, and the presser ring 62 is fastened via the packing gland 65, whereby the waterproof packing 66 is crushed and compressed.

By adoption of the configuration as above, the connector 5 can ensure watertightness around the respective contact point pins 31a and 33a in the electric plug portion 28 which is an outer sheath easily with a stable structure. Consequently, watertightness of the respective contact point pins 31a and 33a and the electric plug portion 28 can be ensured by the waterproof packing 66 being crushed. Therefore, filling and cure of the filling material or the like as in the conventional configuration are not needed, and the connector 5 can be assembled more easily. Further, the connector 5 has the advantage that the quality variation due to coating variations of the filling material hardly occurs.

Further, in the structure which compresses and fixes the waterproof packing 66 which is an elastic member as in the present embodiment, if the packing gland 65 which is a pressing member which compresses the waterproof packing 66 is fixed by being pressed by a part of the support plate 61 which is a frame, the compression amount of the waterproof packing 66 is likely to vary due to assembly tolerance variations of the respective components. Meanwhile, if the pressing mechanism for the waterproof packing 66 is provided separately from the support plate 61, the entire structure is upsized.

However, the structure of the connector 5 of the present embodiment is the structure in which the support plate 61 is first fixed to the electric plug portion 28, the presser ring 62 is fastened to the support plate 61, and the waterproof packing 66 is compressed by the packing gland 65. Thereby, the mechanical tolerance variation of the support plate 61 can be absorbed by the fastening amount of the presser ring 62, and the compression amount of the waterproof packing 66 is hardly influenced by the component assembly tolerance variation of the support plate 61. Accordingly, the advantage is provided, that the pressing structure which compresses the support plate 61 and the waterproof packing 66 can be configured with space-saving irrespective of cumulative intersection tolerance in the axial direction of the support plate 61.

As above, the support plate 61 is fixed to the electric plug portion 28, the presser ring 62 is fastened, and the waterproof packing 66 is compressed, after which, a first board 71 which is a disk-shaped electric board is assembled as shown in FIG. 9. On the first board 71, a positioning hole portion 71a in a center, a plurality of through lands 71b arranged in an arc shape along a board surface edge, and hole portions 71c through which the respective components are inserted are formed, and various electronic components are mounted.

In the first board 71, the end portions of the plurality of first contact point pins 31a which are vertically installed in the recessed portion 28a of the electric plug portion 28 are inserted in the plurality of through lands 71b respectively. Subsequently, in a state in which the first board 71 is supported by the respective first contact point pins 31a, the plurality of through-lands 71b and the plurality of first contact point pins 31a are soldered to one another. The screw receiving pipes 63 and the like are disposed in the hole portions 71c of the first board 71 in a state loosely inserted therein.

At this time, even though the first board 71 is in the state soldered to the plurality of first contact point pins 31a, the plurality of first contact point pins 31a which are supported are vertically installed in the recessed portion 28a of the electric plug portion 28 with a predetermined length, and therefore, the position thereof is in the state freely movable within the range of the loose insertion of the screw receiving pipes 63 and the like in the hole portions 71c and within the range of the elasticity of the first contact point pin 31a.

In the first board 71, a pin 70 which is an axial aligning shaft body and is a positioning member of the present embodiment is inserted and fitted in the positioning hole portion 71a formed in a center. The pin 70 is fitted in the screw hole 61b formed in the center of the support plate 61 in a state in which the pin 70 is inserted and fitted in the positioning hole portion 71a.

As above, the first board 71 is electrically connected to the plurality of first contact point pins 31a, after which, the first board 71 is positioned in the axial direction orthogonal to the board surface by the pin 70, and the installed position into the electric plug portion 28 is defined. Like this, in the conventional connector, electric connection and mechanical fixation are needed when the electric board is assembled, and mechanically fixed position precision is difficult to obtain since electrical connection is generally given priority, whereas the connector 5 of the present embodiment is configured such that after the first board 71 is soldered to the plurality of first contact point pins 31a, the pin 70 which is a axially aligning member which restricts the axial direction of the first board 71 is fitted therein, and thereby the position of the first board 71 is restricted.

Therefore, the first contact point pins 31a are disposed in such a manner as to be vertically installed with the predetermined length in the electric plug portion 28 so that axial alignment of the first board 71 can be performed within the range of the elasticity of the first contact point pins 31a by using the elasticity of the first contact point pins 31a. As a result, the connector 5 of the present embodiment has the advantage of being capable of enhancing the assembly position precision of the first board 71 while ensuring electric connection of the first board 71.

Subsequently, a second board 72 which is an electric board in a disk shape with an outside diameter larger than the first board 71 is assembled to the electric plug portion 28 in which the first board 71 is installed, as shown in FIG. 10. On the second board 72, a plurality of through lands 72a and 72b, a cutout portion 72c in an arc shape which is formed outward of the plurality of through lands 72b, and hole portions 72d through which respective components are inserted are formed, and various electronic components are mounted, as shown in FIG. 11.

Further, in the second board 72, two different patient circuit pattern areas 73 and 74 are placed to divide the surface. On the first patient circuit pattern area 73 which is one of the pattern areas, the plurality of through lands 72a are placed, whereas on the second patient circuit pattern area 74 which is the other pattern area, the plurality of through lands 72b are placed. Between the first patient circuit pattern area 73 and the second patient circuit pattern area 74, a non-patternable area 75 is formed to have a predetermined space (width) La.

This is based on the rule that when two or more different patient circuit patterns are formed on one board, the clearance or the creepage distance on the board that is defined by the IEC (International Electrotechnical Commission) standards, in order to ensure basic insulation between the different patient circuits.

Consequently, the second board 72 of the present embodiment has the two different patient circuit pattern areas 73 and 74, and has the non-patternable area 75 for providing insulation between the two patient circuit pattern areas 73 and 74 formed therein.

Further, in the second patient circuit pattern area 74 of the second board 72, the cutout portion 72c in an arc shape is formed outward of the plurality of through lands 72b. This brings about the advantage of being able to make a separation distance from the member electrically continuing to the first patient circuit pattern area 73 shorter than the predetermined space (width) La of the non-patternable area 75 provided to ensure the creepage distance on the board, because the distance with which basic insulation for the first patient circuit pattern area 73 is ensured can be calculated by an air clearance by the cutout portion 72c being provided on the second patient circuit pattern area 74.

More specifically, the second patient circuit pattern area 74 becomes an area which can ensure basic insulation from the first patient circuit pattern area 73 by the clearance of the cutout portion 72c in an outer circumferential edge portion of the second board 72. Therefore, a ground member and the like which electrically continue to the first patient circuit pattern area 73 can be disposed on an outer circumferential side of the second board 72 at which the second patient circuit pattern area 74 is provided.

The ground member which electrically continues to the first patient circuit pattern area 73 is the flange portion 25 of the disk-shaped metal frame 20 in the present embodiment, as will be described later.

As above, the second board 72 can obtain the air clearance from the first patient circuit pattern area 73 by formation of the cutout portion 72c on the second patient circuit pattern area 74, and therefore, basic insulation can be ensured with a shorter distance. Therefore, the second board 72 has the advantage of being able to prevent upsizing and achieve space saving of the board itself as compared with the case of ensuring the IEC standards by the creepage distance on the board which requires a space larger than the air clearance.

Here, the configuration of the second board 72 is described, and the technique of forming the cutout portion 72c for ensuring basic insulation between the patient circuit pattern areas is also applicable to the first board 71 as a matter of course.

In the second board 72 which is configured as above, the end portions of the plurality of second contact point pins 33a which are vertically installed in the recessed portion 28a of the electric plug portion 28 are inserted in the plurality of through lands 72a and 72b. Subsequently, in the state in which the second board 72 is supported by the respective second contact point pins 33a, the plurality of through lands 72a and 72b and the plurality of second contact point pins 33a are soldered to one another. In this case, the screw receiving pipes 63 and the like are also disposed in the hole portions 72d of the second board 72 in a state loosely inserted therein.

At this time, the second board 72 is in the state in which the position thereof is freely movable within the loose insertion range of the screw receiving pipes 63 and the like in the hole portions 72d and the range of the elasticity of the second contact point pins 33a, because even in the state in which the second board 72 is soldered to the plurality of second contact point pins 33a, the plurality of second contact points pin 33a which support the second board 72 are vertically installed in the recessed portion 28a of the electric plug portion 28 with the predetermined length, similarly to the first board 71.

Subsequently, the disk-shaped metal frame 20 is fitted onto the electric plug portion 28 in such a manner as to cover the second board 72 as shown in FIG. 12. At this time, the flange portion 25 of the disk-shaped metal frame 20 is butted to the outer circumferential end portion of the electric plug portion 28, the three fixing screws 63a which are fixing members are screwed into the screw receiving pipes 63 from the front side, and the electric plug portion 28 is fixed to the disk-shaped metal frame 20 in a state in which the electric plug portion receives a predetermined compression force. An O-ring for keeping airtightness (watertightness) is placed between the electric plug portion 28 and the flange portion 25. Further, the screw receiving pipe 63 includes such a length that the end portion thereof which faces the disk-shaped metal frame 20 does not abut on the disk-shaped metal frame 20 so that the electric plug portion 28 generates a predetermined compression force to the disk-shaped metal frame 20.

Further, a part of an inner surface of the flange portion 25 is brought into a state in contact with an outer circumferential surface of the second board 72. More specifically, the second board 72 which can move its position freely within the range of elasticity of the second contact point pins 33a, and within the loose insertion range of the screw receiving pipes 63 and the like in the hole portions 72d has the outer circumferential surface fitted to part of the inner surface of the flange portion 25 by being in contact with the part of the inner surface of the flange portion 25, and is positioned in the axial direction orthogonal to the board surface, and the installed position in the electric plug portion 28 is defined.

As above, the second board 72 is configured such that after the second board 72 is soldered to the plurality of second contact point pins 33a, the flange portion 25 of the disk-shaped metal frame 20 is fitted onto the electric plug portion 28, and thereby, the position thereof is defined.

Consequently, the second contact point pins 33a are disposed to be vertically installed in the electric plug portion 28 with the predetermined length so that with use of the elasticity of the second contact point pins 33a, the second board 72 can be axially aligned within the range of the elasticity. As a result, the connector 5 of the present embodiment has the advantage of being able to enhance assembly position precision of the second board 72 while also ensuring electric connection in the second board 72.

Furthermore, a ground layer is formed on the entire board surface in the disk-shaped second board 72. Incidentally, in order to enhance electromagnetic shield performance in the connector 5, it is effective to cover the entire body with a shield member, but if the configuration of covering the entire body with a shield member is adopted, the number of components is increased, and cost increase, complication of assembly and the like are caused. However, the ground layer is formed on the entire second board 72 of the present embodiment, whereby the various electronic components placed in the first board 71 and the second board 72 disposed in the electric plug portion 28 are brought into the state covered with a lid by the ground layer.

Consequently, only the shield member has to be installed on only a side surface substantially of a cylinder inside the connector 5 of the present embodiment in a substantially cylindrical shape. Consequently, the connector 5 is prevented from being increased in the number of components while ensuring shield performance for EMC measure.

As described above, in the connector 5 of the present embodiment, the proximal end portion (A portion of FIG. 6) which is at the electric plug portion 28 side to which the disk-shaped metal frame 20 is fitted and fixed is assembled as shown in FIG. 13. In the assembly state, the disk-shaped metal frame 20 having the flange portion 25 serves as the strength frame member, the disk-shaped metal frame 20 and the electric plug portion 28 generate compression force by the fixing force of the three fixing screws 63a, reaction force to the aforesaid compression force is generated in the axis (axis along the longitudinal direction) direction in the front-back direction, and a firm block structure with the entire strength more enhanced is provided.

The light guide pipe sleeve 26 is formed by combination of a plurality of tubular members, and inside the tubular members, a cover glass 45, a rod lens 46 connectively provided at the cover glass 45, and a light guide bundle 47 which is a light guide fiber bundle a terminal end of which is disposed close to the rod lens 46 are placed from a proximal end side.

Further, a light guide insertion tube body 48 is inserted, fitted and fixed to the light guide pipe sleeve 26 from a distal end side which is at the electric plug portion 28 side. The light guide insertion tube body 48 includes such a length that a distal end portion projects from the disk-shaped metal frame 20, and is formed of a metal pipe with excellent slidability, or a PTFE tube so that insertability of the light guide bundle 47 is not reduced.

The light guide insertion tube body 48 is placed to solve the problems that when the light guide bundle 47 which is a light transmission member is inserted through the light guide pipe sleeve 26 in assembly of the connector 5, if the insertion portion of the light guide pipe sleeve 26 is located in an inner position in the inside of the electric plug portion 28 or the like, operability is extremely bad, and if the end surface of the light guide bundle 47 is brought into contact with the other members, the light guide end surface is damaged (see FIG. 13).

More specifically, the operation of inserting the light guide bundle 47 through the component located in an inner position is difficult because visual check cannot be made, but at the time of assembly of the connector 5, an operator can visually check the member close to the operator, and therefore, the configuration is provided, which facilitates the operation of inserting the light guide bundle 47. Therefore, reduction in operability as the result that the end surface of the guide bundle 47 is caught by the edge portion of the member through which the guide bundle 47 is inserted is restrained.

Thereby, the connector 5 of the present embodiment has the configuration in which the light guide insertion tube body 48 including such a length that the distal end portion projects from the disk-shaped metal frame 20 is joined to the light guide pipe sleeve 26 to be extended to the position where the operator can make visual check. Accordingly, the connector 5 is configured to enhance assembly operability because the insertion operation of the light guide bundle 47 into the light guide pipe sleeve 26 in the state in which visual check cannot be made is eliminated.

Next, a configuration of the front side (B portion of FIG. 6) of the connector 5 will be described in detail below based on the assembly state of the respective components with use of FIGS. 14 to 16.

As shown in FIGS. 14 to 16, a metal main frame member 50 is fixedly attached to the disk-shaped metal frame 20 by a screw (not illustrated) first. The main frame member 50 has a holder 51 (see FIG. 17) that configures a holding portion which is formed into a recessed portion by a part of an outer circumference of a circular ring at the other end portion at the opposite side from one end portion joined to the disk-shaped metal frame 20 being cut out, and holds built-in objects such as the light guide bundle 47, the electric cable and various tubes. A circular ring member 52, which is a separation preventing member, is put on an outer circumferential portion of the holder 51, and the circular ring member 52 is fixedly attached thereto by a plurality of screws. The circular ring member 52 covers the built-in objects housed in the holder 51, and thereby, prevents the built-in objects from separating from the holder 51 and falling off. Further, two screw grooves are formed in a front and a rear in the outer circumference of the circular ring member 52.

A first shield member 53 in a substantially cylindrical shape is fixedly attached to the disk-shaped metal frame 20 by screws 53a.

Next, the end portion (circumferential end surface) of the connector case 23 which houses the first shield member 53 in such a manner as to cover the first shield member 53 is butted to the flange portion 25 of the disk-shaped metal frame 20 from a surface side (front side) opposite from the side where the electric plug portion 28 is joined. At this time, the flange portion 25 is in the state exposed at two locations in the circumferential direction in the end portion of the connector case 23. An O-ring for keeping airtightness (watertightness) is provided at a joining portion of the flange portion 25 and the connector case 23.

Next, a second shield member 54 in a substantially cylindrical shape which has an outer shape analogous to the outer shape of the connector cover 24 and can be housed in the connector cover 24 is assembled. The second shield member 54 is butted to the first shield member 53 to house the main frame member 50.

At this time, the circular ring member 52 is exposed from an opening 54a (see FIG. 14) which is formed at an end portion of the second shield member 54. Subsequently, a ring-shaped shield pressing member 55 which abuts on an end surface of the second shield member 54, and presses the second shield member 54 to be fitted or abut on the first shield member 53 at the rear side (disk-shaped metal frame 20 side) is screwed to the circular ring member 52.

More specifically, the shield pressing member 55 moves in a front-back direction along the axis of the circular ring member 52 in accordance with the screwed amount to the circular ring member 52. Subsequently, the shield pressing member 55 has the screwed amount to the circular ring member 52 regulated to be moved to the rear side, abuts on the end surface around the opening 54a of the second shield member 54, presses the second shield member 54 to the rear side to press the second shield member 54 to be fitted to or abut on the first shield member 53.

Next, the connector cover 24 is assembled in such a manner as to cover the second shield member 54. The connector cover 24 houses the second shield member 54, and is butted so that the rear end portion (circumferential end surface) covers the front end portion of the connector case 23. An O-ring for keeping airtightness (watertightness) is also provided in a joining portion of the connector case 23 and the connector cover 24.

Subsequently, the circular ring member 52 is exposed from the opening 24a (see FIG. 15) formed at the end portion of the connector cover 24. Subsequently, a case fastening ring 56 that is a fixing member which presses the connector cover 24 so that the connector cover 24 is fitted to the connector case 23 at the rear side (disk-shaped metal frame 20 side) is screwed to the circular ring member 52.

The case fastening ring 56 also moves in the front-back direction along the axis of the circular ring member 52 in accordance with the screwed amount to the ring member 52. Subsequently, the case fastening ring 56 has the screwed amount to the circular ring member 52 regulated to move to the rear side, abuts to an end surface of a projected portion 24b which is formed to project in an inside diameter direction in the opening 24a of the connector cover 24 (see FIG. 16), presses the connector cover 24 to the rear side, and presses the connector cover 24 so that the connector cover 24 is fitted to the connector case 23.

Thereby, the connector 5 of the present embodiment has the proximal end portion (B portion of FIG. 6) which is the front side from the disk-shaped metal frame 20 assembled as shown in FIG. 16. In the assembly state, the connector case 23 and the connector cover 24 are compressed in the axis (axis along the longitudinal direction) direction in the front-back direction toward the flange portion 25 of the disk-shaped metal frame 20 which is a strength frame member, and the reaction force to the compression force occurs to the connector case 23 and the connector cover 24, whereby, a firm hollow structure with the entire strength more enhanced is provided.

More specifically, the force which is compressed in the front-back axial direction and is to be expand in the diameter direction orthogonal to the front-back axial direction works on the hollow connector case 23 and connector cover 24. Therefore, stress which is to expand in the diameter direction is generated in the side circumferential surfaces of the connector case 23 and the connector cover 24, and the firm configuration against the external load is provided.

As described above, the connector 5 of the present embodiment is configured to be provided with the disk-shaped metal frame 20 which is the strength frame member, at the intermediate portion, and divided into the firm block structure and the firm hollow structure at the front and the rear with the disk-shaped metal frame 20 therebetween. Thereby, the connector 5 is prevented from being reduced in strength to the external load as a result that the entire length in the front-back direction being long. More specifically, the connector 5 is configured to be more enhanced in strength to external load since the strength structure is divided into two in the longitudinal direction.

Further, in the connector 5, the connector cover 24 which is the outer sheath case of the rear side has the case fastening ring 56 screwed to the circular ring member 52 fixed to the distal end of the main frame member 50 to abut on the circular ring member 52, and thereby, is pressed so that the connector case 23 reliably abuts on and is fitted to the disk-shaped metal frame 20 and the connector cover and the connector case reliably abut on and are fitted to each other in the state in which the connector cover 24 receives compression force with the connector case 23 which is the outer sheath case of the front side. Apart from the above, in the connector 5, the shield pressing member 55 which is screwed to the circular ring member 52 is screwed to and abuts on the second shield member 54 provided inside the connector case 23 and the connector cover 24, and thereby the second shield member 54 is pressed to be fitted or abut on the first shield member 53.

As above, the connector 5 is configured such that the connector case 23 and the connector cover 24 which are outer sheath cases, and the respective shield members 53 and 54 are pressed against different members. As above, the connector 5 has the connector structure which is fixed by the end surfaces of the outer sheath cases butted to each other, has the advantageous structure which ensures strength of the entire connector and eliminates a gap in the outer appearance, and is configured to prevent reduction in shield performance by ensuring butting of the respective shield members 53 and 54 separately from the outer sheath cases. More specifically, the connector 5 is structured such that the structure which pressing the respective shield members 53 and 54 against each other and the structure which presses the outer sheath cases against each other are provided separately, and the respective structures are individually butted to each other. As a result, the connector 5 is configured to be able to reinforce the shield structure by providing the presser of the shield members 53 and 54 as separate pieces. The connector 5 has various components assembled inside before assembly of the respective shield members 53 and 54, the connector case 23 and the connector cover 24 described above.

In the connector 5, the front side is configured by the two outer sheath cases that are the connector case 23 and the connector cover 24, and thereby, in the case of deterioration, breakage or the like, only the outer sheath case where deterioration, damage or the like occurs can be replaced.

Furthermore, in the connector 5, the flange portion 25 of the disk-shaped metal frame 20 is butted to the outer circumferential end portion of the electric plug portion 28, the three fixing screws 63a are screwed into the screw receiving pipes 63 from the front side, the respective shield members 53 and 54 are butted and fixed by fastening of the shield pressing member 55 from the front side, and the connector cover 24 is butted to the connector case 23 side to be fixed by fastening of the case fastening ring 56 from the front side. As above, in the connector 5, fixing of the respective members is performed from the common direction from the front side to the rear side, that is, the directionality of fixing the respective members is the same, and therefore, the connector 5 is configured to be favorable in assembly operability. Further, in the connector 5, the directionality is also the same in disassembly of the respective members, and therefore, maintainability is also enhanced.

Here, various components placed inside the connector 5 will be described in detail hereinafter.

First, the main frame member 50 is formed by cutting of a metal plate block, or a die cast method, and has the holder 51 at one end which is the front side, and a frame connection portion 58 which is fixed to the disk-shaped metal frame 20 by a screw at the other end which is the rear side. An opening 50a is formed in a central portion of the front side, and arm portions 57 are provided at both side portions of the opening 50a. Further, the main frame member 50 has one surface side in which various conduits and the like are placed formed into a recessed shape, and a plurality of groove portions 59 in recessed portion shapes and an opening 50b in which various conduits and the like are disposed are formed on one surface formed in the recessed shape toward the rear side from the opening 50a.

In the main frame member 50, the shapes of the respective openings 50a and 50b are formed to achieve reduction in weight with the predetermined required strength (rigidity) being ensured.

Subsequently, inside the connector 5, a forward water supply conduit 81 which communicates with the forward water supply pipe sleeve 40, a water supply conduit 82 which communicates with the water supply pipe sleeve 38, a suction conduit 83 which communicates with the suction pipe sleeve 41, and a pressurizing conduit 84 which communicates with the pressurizing pipe sleeve 39 are placed, as shown in FIG. 18.

The respective conduits 81, 82, 83 and 84 are disposed in the predetermined groove portions 59 formed on one surface of the main frame member 50 which is disposed to penetrate through the central portion of the connector 5. Tube connection pipe sleeves 81a, 82a, 83a and 84a are connected to end portions of the respective conduits 81, 82, 83 and 84, and the tube connection pipe sleeves 81a, 82a, 83a and 84a are disposed in a position of the opening 50a of the main frame member 50.

A forward water supply tube 81c, a water supply tube 82c, a suction tube 83c and a pressurizing tube 84c which are inserted through and disposed in the universal cable 4 are connected to the respective tube connection pipe sleeves 81a, 82a, 83a and 84a as shown in FIG. 19. Tube connectors 81b, 82b, 83b and 84b for connecting airtightly (watertightly) to correspond to the tube connection pipe sleeves 81a, 82a, 83a and 84a are placed at the respective end portions of the respective tubes 81c, 82c, 83c and 84c. At this time, the aforementioned light guide bundle 47 is also inserted through the light guide insertion tube body 48 and fixed.

Further, the respective tubes 81c, 82c, 83c and 84c and the light guide bundle 47 are housed in the state bundled in the holder 51 in the U-shape, and thereafter, the circular ring member 52 is fixed to the holder 51. Though not illustrated here, electric board boxes are disposed on both surfaces of the main frame member 50.

As above, the connector 5 has the complicated structure inside with the presence of the respective conduits 81, 82, 83 and 84, the respective tubes 81c, 82c, 83c and 84c, the light guide bundle 47 for optical transmission, the boxes of the electric system and the like. Therefore, the connector 5 of the present embodiment can have the compact configuration by having the main frame member 50 for ensuring strength disposed, having the respective conduits 81, 82, 83 and 84 disposed in the plurality of groove portions 59 in the recessed portion shapes, having one surface of the main frame member 50 formed into the recessed portion, and having the running space for the respective tubes 81c, 82c, 83c and 84c, the light guide bundle 47 for optical transmission, the cables of the electric systems and the like ensured.

Thereby, even if the main frame member 50 for enhancing strength is provided in the connector 5, the disposition space for the built-in objects does not become narrow, the respective components do not become hindrance, and reduction in assembly operability can be prevented, by ensuring the running space.

Furthermore, the opening 50a is formed in the main frame member 50, so that the respective conduits 81, 82, 83 and 84 and the respective tubes 81c, 82c, 83c and 84c can be connected in the position of the opening 50a. Thereby, when the tube connection pipe sleeves 81a, 82a, 83a and 84a of the respective conduits 81, 82, 83 and 84 are connected to the tube connectors 81b, 82b, 83b and 84b of the respective corresponding tubes 81c, 82c, 83c and 84c in the connector 5, connection is performed in the position of the opening 50a, and therefore, reduction in operability and maintainability is prevented without hindrance of the main frame member 50.

From the above description, in the connector 5 of the present embodiment, the running space for the piping system, the optical system, the electric system and the like can be used in common with respect to the main frame member 50 which is the strength member, and therefore, the structure of the inside can be made compact. The main frame member 50 is provided in the central portion of the connector, and does not become hindrance at the time of making access to the respective systems, and the operability and maintainability are enhanced.

Incidentally, the water supply pipe sleeve 38, the pressurizing pipe sleeve 39, the forward water supply pipe sleeve 40, the suction pipe sleeve 41 and the like are placed in the connector case 23 which is the outer sheath case of the connector 5 and is formed of a synthetic resin, plastic or the like. In the connector case 23, the first shield member 53 is placed. In the first shield member 53, the hole portions for passing the respective pipe sleeves 38, 39, 40 and 41, or the respective conduits 81, 82, 83 and 84 which communicate with the pipe sleeves 38, 39, 40 and 41 have to be formed. Therefore, gaps are formed between the respective pipe sleeves 38, 39, 40 and 41, or the respective conduits 81, 82, 83 and 84, and the hole portions of the first shield member 53, and internal and external electromagnetic waves are likely to leak.

Thus, in the present embodiment, the gaps from the hole portions provided in the first shield member 53 for the respective pipe sleeves 38, 39, 40 and 41 are covered with a metal, and the shield performance of the connector 5 is ensured. Here, as shown in FIG. 20, for example, the suction pipe sleeve 41 will be described specifically as an example.

As shown in FIG. 20, the suction pipe sleeve 41 which is airtightly (watertightly) held by the O-ring and fixed to the pipe sleeve disposition surface 37 of the connector case 23 has a metal pipe sleeve member 41a airtightly joined at the inner side of the connector case 23. The suction conduit 83 which extends into the connector case 23 is connected and fixed to the metal pipe sleeve member 41a by press-fitting.

The metal pipe sleeve member 41a is inserted through the hole portion of the first shield member 53 and the hole portion of the connector case 23 from the inner side of the connector case 23 to the outer side. The suction pipe sleeve 41 is joined and fixed to the metal pipe sleeve member 41a which projects from the pipe sleeve disposition surface 37 of the connector case 23.

In the state, a flange 41b which blocks the hole portion of the first shield member 53 is formed at the end portion of the metal pipe sleeve member 41a, and the flange 41b is brought into contact with the first shield member 53. More specifically, the suction pipe sleeve 41 and the metal pipe sleeve member 41a are fixed in the state in which the flange 41b is in contact with the hole portion of the first shield member 53 to block the hole portion in such a manner as to sandwich the connector case 23 and the first shield member 53.

Thereby, the flange 41b is disposed to be superimposed on the first shield member 53 to cover the gap formed between the hole portion of the first shield member 53 and the outer circumferential portion of the metal pipe sleeve member 41a. Accordingly, the gaps of the hole portions formed on the first shield member 53 can be completely covered with the metal flange 41b, and therefore, the shield performance of the connector 5 is ensured.

Further, after the piping system, the optical system and the like are disposed in the connector 5, a first and a second shield cases 76 and 77 which house electric boards are provided respectively on both surface sides of the main frame member 50 as shown in FIG. 21. The first and the second shield cases 76 and 77 are electrically connected to each other via a flat cable 78.

Further, the first and the second shield cases 76 and 77 are respectively disposed on both surfaces of the main frame member 50 of a metal, for example, stainless steel as shown in FIG. 22. A board base 79 in a metal plate shape is interposed between the second shield case 77 to be one side and the main frame member 50, and the second shield case 77 is fixed to the main frame member 50 by a screw in the state in which the second shield case 77 abuts on the board base 79. In the state, the board base 79 abuts on the main frame member 50.

Further, the first shield case 76 to be the other side is provided with a plurality of leg portions 76a to avoid the piping system, the optical system and the like disposed in the main frame member 50, and the leg portions 76a are fixed to the main frame member 50 by the screws.

The board base 79 has a larger surface area than the second shield case 77 of one side, and is placed to increase the contact area of the main frame member 50 and the second shield case 77. Thereby, the advantage is provided, that the heat release efficiency of the heat generated in the electric board in the second shield case 77 becomes higher by the board base 79 being assembled between the main frame member 50 and the second shield case 77 than with the area in which the main frame member 50 and the second shield case 77 abut on each other when the second shield case 77 is directly fixed to the main frame member 50.

More specifically, the heat generated in the electric board in the second shield case 77 can be released through a large metal frame which is configured by the main frame member 50, the board base 79 and the disk-shaped metal frame 20 to which the main frame member 50 is joined, and therefore, the heat release efficiency is enhanced. Accordingly, when the connector 5 of the present embodiment releases the heat generated in the electric board installed inside, heat release is performed by the heat transfer effect among the components, and therefore, does not have to use a complicated heat release structure, and therefore, upsizing, increase in cost and the like are prevented.

Further, the first shield case 76 and the second shield case 77 are disposed in parallel to be in the state along the plane of the main frame member 50 with the main frame member 50 therebetween (see FIG. 21). Thereby, the first and the second shield cases 76 and 77 respectively containing the electric boards therein can be compactly housed in the connector 5.

Further, as shown in FIGS. 23 to 26, only the first shield case 76 is provided with an electric connection portion with various electric cables which are placed by being inserted through the inside of the universal cable 4. The electric connection portion of the first shield case 76 is configured by two FPC connectors 91 which are connected to respective terminal ends of first electric cables 91a for exchanging signals of a first electric system, and an electric connector portion 92 which is connected to a terminal end of a second electric cable 92a for exchanging a signal of a second electric system.

Each of the FPC connectors 91 is provided with a heat shrinkable tube 94 for protecting a connection region to each of the first electric cables 91a. The respective FPC connectors 91 are individually connected to two flexible connectors 93 which are provided at the electric board in the first shield case 76 (see FIG. 24 and FIG. 26).

A shield cover 76b is put on the first shield case 76 so as to cover the connection portion of the FPC connectors 91 and the flexible connectors 93. At this time, the heat shrinkable tube 94 is caught by an internal surface of the shield cover 76b, so that removal of the FPC connector 91 from the flexible connector 93 is prevented, and removal of the FPC connector 91 itself is prevented.

As above, the mechanism for preventing removal of the FPC connector 91 is configured such that the heat shrinkable tube 94 which is provided for ensuring shield performance of the connection region of the FPC connector 91 and the first electric cable 91a is caught by the shield cover 76b. Therefore, an extra space is not required for a removal preventing component, and cost increase, complication of an assembly operation and the like due to increase in the number of components and the like are also prevented. More specifically, the first shield case 76 and the FPC connector 91 also include the function of preventing removal, whereby space saving, and reduction in the number of components can be performed.

Further, the electric connector portion 92 includes a connector mount board 68 provided with an electric connector 68a on one surface (bottom surface in this case), and is provided with a metal cover body 69 which is fixed to cover the other surface (top surface in this case) of the connector mount board 68, as shown in FIG. 25. The cover body 69 is electrically continuous with a ground layer of the connector mount board 68.

In the electric connector portion 92, the electric connector 68a is connected to a receiving side connector 67a mounted on an electric board 67 placed in the first shield case 76. From the state, the shield cover 76b is fitted to the first shield case 76 to cover a top surface of the electric connector portion 92.

Further, in the shield cover 76b, a leaf spring 69a which is a metal elastic member is placed on an internal surface opposed to a top surface of the electric connector portion 92, and the leaf spring 69a is brought into contact with the cover body 69 of the electric connector portion 92 to press the cover body 69 to a lower side.

The leaf spring 69a presses the electric connector portion 92 as above, whereby the receiving side connector 67a of the electric board 67 and the electric connector 68a of the connector mount board 68 are reliably connected, and removal of the electric connector portion 92 is prevented. Further, the cover body 69 which is electrically continuous with the ground layer of the connector mount board 68 and the leaf spring 69a abut on each other, whereby electric continuity of the ground of the connector mount board 68 and the first shield case 76 can be ensured.

By the configuration as above, the functions of preventing removal of the connector and reinforcement of ground (shield) can be performed with only the conductive elastic members, and therefore, space saving and reduction of the number of components are enabled.

The configuration may be adopted, in which a ground layer is formed on the top surface of the connector mount board 68, and the leaf spring 69a is in contact with the ground layer to press the ground layer, instead of the cover body 69 being provided.

Further, as shown in FIGS. 27 and 28, the connector mount board 68 is fixedly attached to an access side of the second electric cable 92a by soldering, brazing or the like, and is provided with a fixing metal fitting 95 including a return portion 95a which projects to both sides of an end portion.

First, the connector mount board 68 is provided with a plurality of connection lands 68b on a surface where the electric connector 68a is provided, and element wires of the respective cable wires 92b of the second electric cable 92a are soldered to the connection lands 68b.

Subsequently, the connector mount board 68 has a heat shrinkable tube 96 (see FIG. 28) covering an outer sheath portion of the second electric cable 92a located on the fixing metal fitting 95 as well as the fixing metal fitting 95, and heat is applied to the heat shrinkable tube 96. Thereupon, the heat shrinkable tube 96 shrinks and fixes an outer sheath end portion of the second electric cable 92a as well as the fixing metal fitting 95. At this time, the heat shrinkable tube 96 shrinks in such a manner as to catch the return portion 95a of the fixing metal fitting 95 to fix the second electric cable 92a firmly. In FIG. 28, each of the cable wires 92b of the second electric cable 92a is not illustrated.

The fixing metal fitting 95 and the heat shrinkable tube 96 are provided in the boundary portion of the second electric cable 92a and the connector mount board 68 as above, whereby a burden which is exerted on the second electric cable 92a by stress concentration exerted on the boundary portion can be reduced, and connection strength of the second electric cable 92a and the connector mount board 68 can be enhanced with a simple structure.

Incidentally, the second shield case 77 contains a main board 85, a connector holding board 86 provided with an electric connector 88 at an edge end of a rear side, and an FPC 87 which electrically connects the main board 85 and the connector holding board 86, as shown in FIG. 29. Further, the main board 85 has one surface (bottom surface in this case) side fixed to a shield frame 77a with a plurality of screws 85a.

The shield frame 77a configures a bottom surface portion in the second shield case 77, and a plate-shaped holding portion 77b which holds the connector holding board 86 freely movably at both rear sides is formed. In the plate-shaped holding portion 77b, a hole portion 77c is formed, and of two projected portions 86a and 86b formed at both side end portions of the connector holding board 86, only the projected portion 86a at the front side is loosely fitted in the hole portion 77c. More specifically, the other projected portion 86b of the connector holding board 86 is disposed at a rear side from the holding portion 77b, and is placed in the state in which the connector holding board 86 sandwiches the holding portion 77b with the two projected portions 86a and 86b.

More specifically, the connector holding board 86 on which the electric connector 88 is mounted, and the main board 85 which is fixed to the shield frame 77a with a plurality of screws 85a are connected by the FPC 87, and the connector holding board 86 is configured to be movable forward and backward.

The configuration which connects the connector holding board 86 and the main board 85 via a cable instead of the FPC 87 may be adopted, but use of the FPC 87 enables connection without a connection spot and provides the advantage of suppression of noise, and elimination of need of connection operation.

In the case of connection of the connector holding board 86 and the main board 85 with a cable, the advantage of being able to reduce cost is provided.

The connector holding board 86 is movable forward and backward within the movable range of the projected portion 86a which is loosely fitted in the hole portion 77c of the holding portion 77b, and the projected portion 86a abuts on the edge forming the hole portion 77c, whereby the forward and backward moving range is restricted.

The connector holding board 86 and the main board 85 are substantially entirely covered by a shield lid body 77f configuring the second shield case 77 being put on a top surface side, and the shield lid body 77f and the shield frame 77a being fixed by screws.

In order to restrict movement in the vertical direction of the connector holding board 86 which is movably plated, two elastic bodies 89 of block-shaped rubber, sponge or the like are placed on an inner surface of the rear side of the shield lid body 77f. More specifically, unless the position in the vertical direction of the connector holding board 86 is restricted, the position in the vertical direction of the electric connector 88 is not fixed, and the connector connecting operation is difficult to perform. Therefore, the connector holding board 86 is urged to the lower side by the elastic bodies 89.

Further, in the shield lid body 77f, a cutout portion 77d is formed in a rear edge so as not to inhibit movability in the front-back direction of the electric connector 88. The cutout portion 77d may be provided with a connector pressing portion 77e which is formed to restrict a movable distance of the electric connector 88 and is folded downward so that a proximal end surface of the electric connector 88 abuts thereon when moving rearward.

The second shield case 77 which is configured as above is introduced into the connector 5 along one surface of the main frame member 50 in such a manner that the electric connector 88 is located at the rear side as shown in FIG. 32. Subsequently, the electric connector 88 is connected to the receiving side connector 60 which is mounted on the second board 72 provided in the electric plug portion 28.

At this time, the projected portion 86a of the connector holding board 86 abuts on the edge of the front side of the holding portion 77b which forms the hole portion 77c as the result that the second shield case 77 is pressed in. Therefore, the electric connector 88 receives the pressing force and is reliably connected to the receiving side connector 60.

Further, when the second shield case 77 is extracted, the projected portion 86a of the connector holding board 86 abuts on the edge of the rear side of the holding portion 77b which forms the hole portion 77c. Therefore, if the second shield case 77 is pulled, the electric connector 88 can be disconnected from the receiving side connector 60.

When the connector pressing portion 77e shown in FIG. 31 is provided, the proximal end surface of the electric connector 88 abuts on the connector pressing portion 77e, and the electric connector 88 receives the pressing force, and therefore, is reliably connected to the receiving side connector 60. As described above, if the second shield case 77 is pulled, the electric connector 88 can be disconnected from the receiving side connector 60.

The second shield case 77 can move forward and backward within the movable range of the connector holding board 86 in the state in which the electric connector 88 and the receiving side connector 60 are connected before the second shield case 77 is fixed to the main frame member 50. Therefore, even a certain variation which occurs due to size variations of the respective components occurs to the fixing position of the second shield case 77 and the main frame member 50, a connection failure of the electric connector 88 and the receiving side connector 60 does not occur.

Further, the second shield case 77 can connect the electric connector 88 to the receiving side connector 60 located at an inner position in the form of the unit in the state housing the main board 85 and the like, the connection operation like this can be performed without use of an exclusive jig or the like, and therefore, the assembly operation is facilitated.

As described above, the connector 5 of the present embodiment is configured such that electric connection with the electric plug portion 28 is made with the main board 85 in the second shield case 77, the connection portion with various electric cables placed inside the universal cable 4 by being inserted through the universal cable 4 is provided in only the first shield case 76, and the first shield case 76 and the second shield case 77 are connected with the flat cable 78, and therefore, electric cable connection operation is simplified.

The invention described in the above embodiment is not limited to the embodiment and modified examples, and various modifications can be carried out in the range without departing from the gist of the invention in the practical phase in addition to the above. Furthermore, the above described embodiment includes the inventions in the various stages, and various inventions can be extracted by arbitrary combination in a plurality of components which are disclosed.

For example, even if some components are deleted from all the components shown in the embodiment, if the problem described can be solved, and the effect described is obtained, the configuration from which the components are deleted can be extracted as the invention.

What is claimed is:

1. A connector for a medical instrument connected to an external device for medical use, the connector comprising:
   a plug portion in which a plurality of electric contact point portions to the external device are placed;
   an outer sheath case connectively provided as a separate piece at the plug portion;
   a sub frame member interposed between the plug portion and the outer sheath case, and having a flange portion which abuts on respective end portions of the plug portion and the outer sheath case;
   a main frame member housed in the outer sheath case and fixed to the sub frame member;
   a first fixing member configured to fix the outer sheath case to the main frame member by fastening such that the outer sheath case is pressed in a longitudinal axis direction of the main frame member; and
   a second fixing member configured to fasten the plug portion to the flange portion,
   wherein:
      the outer sheath case receives reaction force to compression force generated in the longitudinal direction of the main frame member by being butted against the flange portion by fastening of the first fixing member and is fixed to the main frame member and the sub frame member in a state in which the outer sheath case is compressed, and
      the plug portion receives pressure generated by being butted against the flange portion by fastening of the second fixing member and fixed to the sub frame member in a state in which the plug portion is compressed.

2. The connector for a medical instrument according to claim 1, wherein the first and second fixing members fix, the outer sheath case and the main frame member and the sub frame member or the plug portion and the sub frame member by fastening from a same direction.

3. The connector for a medical instrument according to claim 1, wherein the outer sheath case is formed of a first case body and a second case body divided into two as a distal end side and a proximal end side along a longitudinal direction.

4. The connector for a medical instrument according to claim 1, further comprising:
- a plurality of contact point pins electrically continuous with the plurality of electric contact point portions, arranged in the plug portion, and perpendicularly installed to have a predetermined length;
- a board electrically connected to the plurality of contact point pins in a state supported by the plurality of contact point pins; and
- a positioning member fitted to the plug portion to position the board which is allowed to move by elastic deformation of the plurality of contact point pins.

5. The connector for a medical instrument according to claim 1, further comprising:
- a plurality of contact point pins electrically continuous with the plurality of electric contact point portions, arranged in the plug portion, and perpendicularly installed to have a predetermined length; and
- a board electrically connected to the plurality of contact point pins in a state supported by the plurality of contact point pins,
- wherein the board which is allowed to move by elastic deformation of the plurality of contact point pins is positioned by a side surface being in surface-contact with an internal surface of the flange portion.

6. The connector for a medical instrument according to claim 1, wherein the main frame member includes a recessed portion for disposing a built-in object, on one surface side.

7. The connector for a medical instrument according to claim 6, wherein the main frame member includes an opening in a position where a connector of the built-in object is disposed.

8. The connector for a medical instrument according to claim 6, wherein the main frame member includes a holding portion which houses and holds the built-in object at another end portion at an opposite side from one end portion fixed to the sub frame member.

9. The connector for a medical instrument according to claim 8, further comprising:
- a separation preventing member which is fixed to cover the holding portion, and is for preventing the built-in object housed and held from being separated from the holding portion.

10. The connector for a medical instrument according to claim 9, wherein the first fixing member which abuts on one end portion of the outer sheath case and fastens the one end portion to a side of the flange portion is screwed into the separation preventing member.

* * * * *